US010089768B2

(12) United States Patent
Otsuka et al.

(10) Patent No.: US 10,089,768 B2
(45) Date of Patent: Oct. 2, 2018

(54) IMAGE PROCESSING DEVICE, IMAGE PROCESSING METHOD, IMAGE PROCESSING PROGRAM, AND IMAGING SYSTEM

(71) Applicant: OLYMPUS CORPORATION, Tokyo (JP)

(72) Inventors: Takeshi Otsuka, Tokyo (JP); Yoichi Yaguchi, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 106 days.

(21) Appl. No.: 15/410,184

(22) Filed: Jan. 19, 2017

(65) Prior Publication Data
US 2017/0132824 A1 May 11, 2017

Related U.S. Application Data

(63) Continuation of application No. PCT/JP2015/070323, filed on Jul. 15, 2015.

(30) Foreign Application Priority Data

Jul. 22, 2014 (JP) ................................ 2014-149145

(51) Int. Cl.
*G06K 9/00* (2006.01)
*G06T 11/60* (2006.01)
(Continued)

(52) U.S. Cl.
CPC .............. *G06T 11/60* (2013.01); *G06T 5/002* (2013.01); *G06T 5/20* (2013.01); *G06T 7/90* (2017.01);
(Continued)

(58) Field of Classification Search
CPC ............. G06K 9/0014; G06K 9/00134; G06K 9/2018; G06K 9/4652; G06T 2207/10024; G06T 7/90
See application file for complete search history.

(56) References Cited

U.S. PATENT DOCUMENTS 4,866,526 A * 9/1989 Ams ........................ A61B 1/05
348/364
6,256,073 B1 * 7/2001 Pettitt ................... H04N 9/3114
348/742
(Continued)

FOREIGN PATENT DOCUMENTS

JP    2000-299874 A    10/2000
JP    2007-257287 A    10/2007
(Continued)

OTHER PUBLICATIONS

International Search Report dated Oct. 6, 2015 issued in PCT/JP2015/070323.

*Primary Examiner* — Li Liu
(74) *Attorney, Agent, or Firm* — Scully, Scott, Murphy & Presser, P.C.

(57) ABSTRACT

An image processing device includes: a reference image selector configured to select one image of an image group as a reference image; a processing target image selector configured to select, as a processing target image, each of images of the image group other than the reference image; an arrangement order setting unit configured to set arrangement order of the images included in the image group; a conversion information estimation unit configured to estimate conversion information between the images adjacent to each other; a deformed image creation unit configured to create a deformed image by subjecting the processing target image to an image conversion using the conversion information cumulatively from the processing target image to the
(Continued)

reference image in the arrangement order; and a color image creation unit configured to create a color image using the deformed images created based on the respective images and the reference image.

16 Claims, 17 Drawing Sheets

(51) Int. Cl.
- *H04N 1/60* (2006.01)
- *G06T 5/00* (2006.01)
- *G06T 7/90* (2017.01)
- *G06T 5/20* (2006.01)

(52) U.S. Cl.
CPC . *H04N 1/6027* (2013.01); *G06T 2207/10016* (2013.01)

(56) References Cited

U.S. PATENT DOCUMENTS

| | | | |
|---|---|---|---|
| 2005/0219518 A1* | 10/2005 | Korngut | G01N 21/47 356/237.2 |
| 2007/0268377 A1* | 11/2007 | Nagano | H04N 9/045 348/222.1 |
| 2009/0002505 A1* | 1/2009 | Imada | H04N 9/045 348/218.1 |
| 2009/0245692 A1 | 10/2009 | Okutomi et al. | |
| 2010/0172020 A1* | 7/2010 | Price | G02B 21/0016 359/381 |
| 2015/0112135 A1 | 4/2015 | Hirota et al. | |

FOREIGN PATENT DOCUMENTS

| | | |
|---|---|---|
| JP | 2008-244833 A | 10/2008 |
| JP | 2014-008142 A | 1/2014 |
| JP | 2014-045275 A | 3/2014 |

* cited by examiner

IMAGE PROCESSING DEVICE, IMAGE PROCESSING METHOD, IMAGE PROCESSING PROGRAM, AND IMAGING SYSTEM

CROSS-REFERENCE TO RELATED APPLICATION

This application is a continuation of PCT international application Ser. No. PCT/JP2015/070323 filed on Jul. 15, 2015 which designates the United States, incorporated herein by reference, and which claims the benefit of priority from Japanese Patent Applications No. 2014-149145, filed on Jul. 22, 2014, incorporated herein by reference.

BACKGROUND OF THE INVENTION

1. Field of the Invention

The present disclosure relates to an image processing device, an image processing method, an image processing program, and an imaging system that correct color deviation in a multiband image captured using a frame sequential method.

2. Description of the Related Art

As a method of generating a color image, a method of combining a plurality of images (multiband images) acquired by capturing images in respective wavelength bands is known.

As a method of capturing the multiband images, a frame sequential method is known. The frame sequential method is a method of capturing images in such a manner that a filter wheel in which a plurality of bandpass filters is arranged is disposed in front of a camera, and the filter wheel is rotated, whereby the images are sequentially captured through the respective bandpass filters.

Meanwhile, chromatic aberration typically occurs in a lens due to different focal positions that depend on colors of beams of light that pass through the lens. This is caused by the fact that a refractive index of a substance varies in accordance with a wavelength of light. More specifically, a phenomenon occurs, that is, a position of an image surface is displaced in a front-back direction on an optical axis in accordance with the wavelength band, or the size of an image varies. For example, assuming that a position of a green image surface is a reference, an image of blue having a shorter wavelength than green is formed on a side close to the lens, and an image of red having a longer wavelength than green is formed on a side far from the lens. Therefore, in a case where the above-mentioned multiband images are combined to generate the color image, images of the same object are displaced in accordance with the colors, that is, so-called color deviation occurs.

In order to solve such a problem, for example, JP 2000-299874 A discloses a technique for correcting the color deviation. Specifically, an edge in an image is extracted by means of the Laplacian operation that performs a second order differential, and a chromatic aberration amount of each color component is calculated based on the edge. Furthermore, a position adjustment is performed between images of the different color components based on a chromatic aberration characteristic curve calculated from the chromatic aberration amount, whereby the color deviation is corrected.

JP 2008-244833 A also discloses a technique for correcting the color deviation. Specifically, a correction table in which pieces of chromatic aberration characteristic data for respective wavelength bands are stored is prepared in advance, and a position adjustment between images in the respective wavelength bands, that is, spectral images, is performed based on the pieces of chromatic aberration characteristic data read from the correction table, whereby the color deviation is corrected.

SUMMARY OF THE INVENTION

An image processing device according to one aspect of the present disclosure includes: a reference image selector configured to select one image of an image group as a reference image, the image group including four or more images generated in such a manner that an object is sequentially captured separately in four or more different wavelength bands; a processing target image selector configured to select, as a processing target image, each of a plurality of images of the image group other than the reference image; an arrangement order setting unit configured to set arrangement order of the images included in the image group such that at least the wavelength bands at the time of capturing the images or positions in capturing order are adjacent to each other between the adjacent images; a conversion information estimation unit configured to estimate conversion information between the images adjacent to each other when the images included in the image group are arrayed in the arrangement order; a deformed image creation unit configured to create a deformed image by subjecting the processing target image to an image conversion using the conversion information cumulatively from the processing target image to the reference image in the arrangement order; and a color image creation unit configured to create a color image using a plurality of the deformed images created based on the respective plurality of images and the reference image.

The above and other features, advantages and technical and industrial significance of this disclosure will be better understood by reading the following detailed description of presently preferred embodiments of the disclosure, when considered in connection with the accompanying drawings.

DETAILED DESCRIPTION OF THE PREFERRED EMBODIMENTS

Hereinafter, embodiments of an image processing device, an image processing method, an image processing program, and an imaging system according to the present disclosure will be described in detail with reference to the drawings. The present disclosure is not limited by these embodiments. In the different drawings, identical elements are provided with the same reference signs.

First Embodiment

Figure 1:
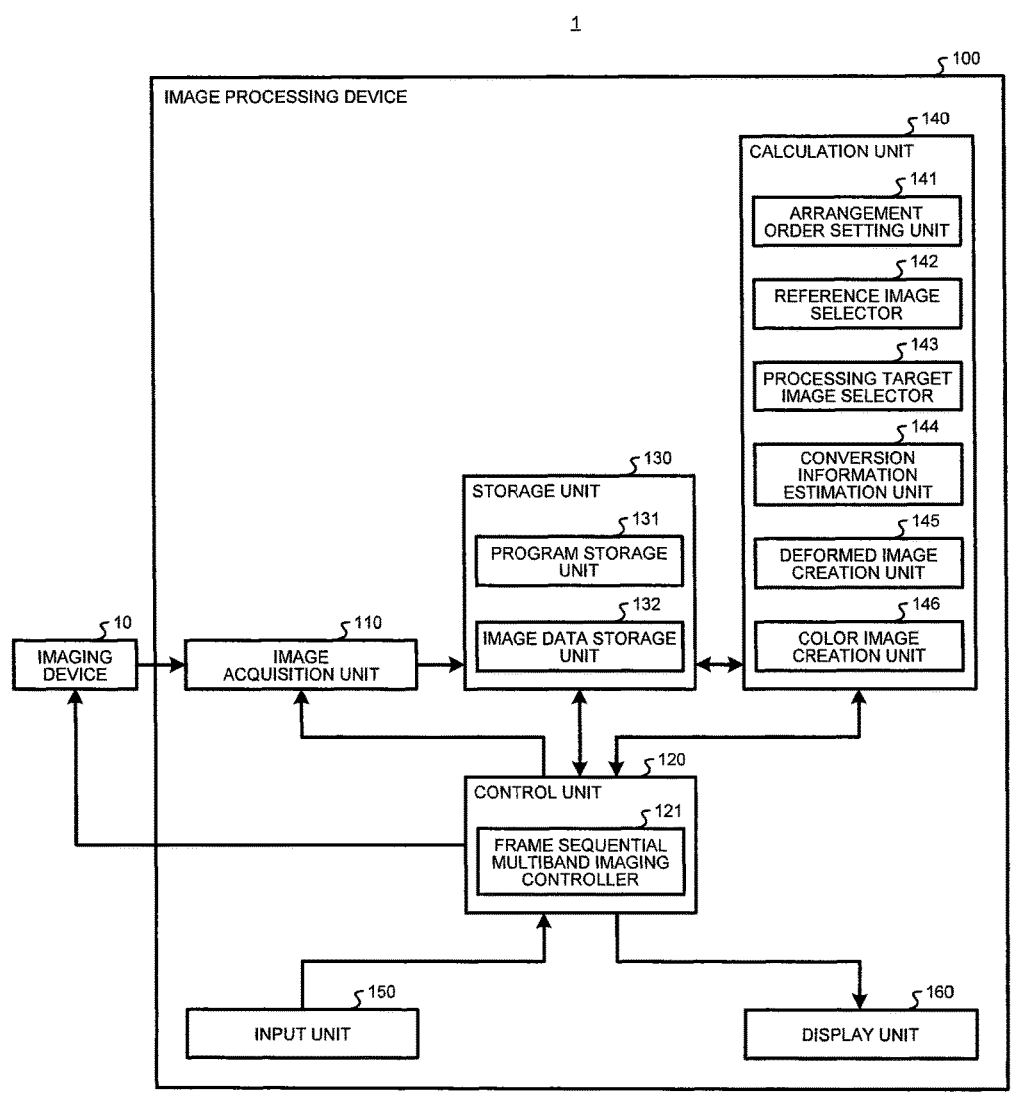
FIG. 1 is a block diagram illustrating an exemplary configuration of an imaging system according to a first embodiment of the present disclosure.

FIG. 1 is a block diagram illustrating an exemplary configuration of an imaging system according to a first embodiment of the present disclosure. As illustrated in FIG. 1, the imaging system 1 according to the first embodiment includes an imaging device 10 and an image processing device 100. The imaging device 10 performs multiband imaging using a frame sequential method to generate an image. The image processing device 100 generates a color image based on the image output from the imaging device 10. In the present application, for the multiband imaging, an object is captured in each of four or more wavelength bands into which a visible light region is separated.

Figure 2:
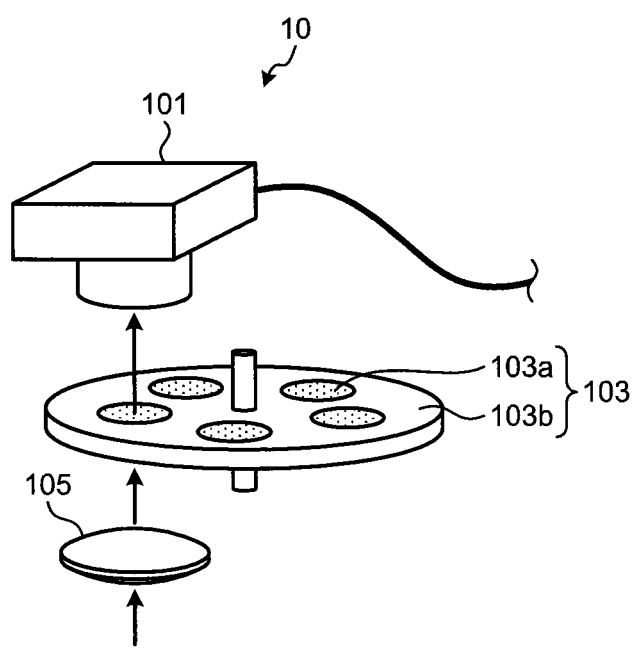
FIG. 2 is a schematic diagram illustrating an exemplary configuration of an imaging device illustrated in FIG. 1.

FIG. 2 is a schematic diagram illustrating an exemplary configuration of the imaging device 10. As illustrated in FIG. 2, the imaging device 10 includes a monochrome camera 101, a filter unit 103, and a tube lens 105. The monochrome camera 101 includes, for example, an imaging sensor such as a CCD and a CMOS, and converts light that has entered a light receiving surface of the imaging sensor into an electric signal that depends on the intensity of the light to output the electric signal as image data.

The filter unit 103 includes a plurality of optical filters 103a and a filter wheel 103b. The plurality of optical filters 103a has different spectral characteristics. The filter wheel 103b rotatably holds the optical filters 103a. The filter wheel 103b is rotated, whereby the optical filter 103a disposed in front of the monochrome camera 101 is sequentially switched. Although the filter unit 103 including five types of the optical filters 103a is illustrated in FIG. 2, the configuration of the optical filters 103a is not limited to this example. For example, a filter unit having 33 optical filters configured such that a center wavelength of the wavelength band shifts by 10 nm between 400 nm to 720 nm may be used.

The tube lens 105 forms an image of observation light from the object (e.g., reflected light from the object) on the light receiving surface of the monochrome camera 101.

When the multiband imaging is performed, the object is irradiated with white light, and images are captured while the optical filter 103a disposed in front of the monochrome camera 101 is switched in accordance with a capturing frame rate. Consequently, the beams of observation light from the object sequentially enter the monochrome camera 101 through the tube lens 105 and the optical filters 103a, and images in wavelength bands corresponding to the respective optical filters 103a are sequentially generated. The imaging device 10 sequentially outputs pieces of image data representing the images in the respective wavelength bands generated in this manner.

The above-mentioned imaging device 10 is provided, for example, in a microscope device, and captures, as the object, a specimen or the like placed on a stage of the microscope device. Alternatively, the imaging device 10 may be provided in an endoscope that is inserted into a living body to capture the inside of a lumen of the living body.

The configuration of the imaging device 10 is not limited to the configuration illustrated in FIG. 2. For example, a liquid crystal tunable filter, a spectral characteristic of which varies by means of electric control, may be used in place of the filter unit 103.

Instead of irradiating the object with the white light, the images in the respective wavelength bands may be generated in such a manner that the object is sequentially irradiated with beams of light in limited wavelength bands, and beams of reflected light from the object are received by the monochrome camera 101 through the tube lens 105.

Referring again to FIG. 1, the image processing device 100 includes an image acquisition unit 110, a control unit 120, a storage unit 130, a calculation unit 140, an input unit 150, and a display unit 160. The image acquisition unit 110 acquires image data of an image group including images in a plurality of wavelength bands. The control unit 120 controls operation of the image processing device 100 and the entire imaging system 1. The storage unit 130 stores the image data or the like acquired by the image acquisition unit 110. The calculation unit 140 executes a predetermined image process based on the image data stored in the storage unit 130.

The image acquisition unit 110 is appropriately configured in accordance with an aspect of the imaging system 1 including the image processing device 100. For example, as illustrated in FIG. 1, in a case where the imaging device 10 is connected to the image processing device 100, the image acquisition unit 110 includes an interface that takes in the image data output from the imaging device 10. In a case where a server in which the image data generated by the imaging device 10 are saved is installed, the image acquisition unit 110 includes a communication device or the like connected to the server, and performs data communication with the server to acquire the image data. Alternatively, the image acquisition unit 110 may include a reader device to which a portable recording medium is detachably attached, and that reads the image data recorded in the recording medium.

The control unit 120 includes, for example, hardware such as a CPU, and reads various control programs stored in the storage unit 130. Consequently, the control unit 120, for example, gives an instruction or transfers data to each component constituting the image processing device 100 in accordance with the image data acquired by the image acquisition unit 110 or various signals input from the input unit 150. The control unit 120 thus comprehensively controls the operation of the image processing device 100 and the entire imaging system 1. In addition, the control unit 120 includes a frame sequential multiband imaging controller 121 that controls the multiband imaging operation with the use of the frame sequential method in the imaging device 10.

The storage unit 130 includes, for example, an information recording device and a reading device therefor. Examples of the information recording device include: various IC memories such as a ROM, e.g., a flash memory capable of updated recording, and a RAM; a built-in hard disk or a hard disk connected by a data communication terminal; or a CD-ROM. The storage unit 130 includes a program storage unit 131 and an image data storage unit 132 to store data or the like that are used during the execution of an image processing program. The program storage unit 131 stores various programs such as the various control programs for controlling the operation of the image processing device 100 and the imaging system 1, and the image processing program that causes the calculation unit 140 to execute an image process for generating a color image based on multiband images. The image data storage unit 132 stores the image data output from the imaging device 10.

The calculation unit 140 is realized by hardware such as a CPU, and reads the image processing program stored in the program storage unit 131. Consequently, the calculation unit 140 executes the image process for generating the color image based on the image data stored in the image data storage unit 132.

More specifically, the calculation unit 140 includes an arrangement order setting unit 141, a reference image selector 142, a processing target image selector 143, a conversion information estimation unit 144, a deformed image creation unit 145, and a color image creation unit 146.

The arrangement order setting unit 141 sets, for the image group including the images in the four or more wavelength bands in which the object is photographed, arrangement order of the images so that the wavelength bands are adjacent to each other between the adjacent images. Hereinafter, the image group including the images in the four or more wavelength bands in which the object is photographed is also referred to as a multiband image group.

The reference image selector 142 selects one image of the multiband image group as a reference image.

The processing target image selector 143 sequentially sets images of the multiband image group other than the reference image as processing target images.

The conversion information estimation unit 144 estimates conversion information (conversion parameter) between the images that are adjacent to each other when the images included in the multiband image group are arranged in the arrangement order set by the arrangement order setting unit 141. Specific examples of an image conversion include any of a non-rigid conversion, a plane projection conversion, an affine conversion, a linear conversion, a scale conversion, a rotation conversion, and a translation, or combinations of these conversions.

The deformed image creation unit 145 creates a deformed image of the processing target image by performing the image conversion using the items of conversion information cumulatively from the processing target image to the reference image in the arrangement order set by the arrangement order setting unit 141.

The color image creation unit 146 creates a color image using the respective deformed images created from all the images included in the multiband image group other than the reference image and the reference image.

The input unit 150 includes, for example, various input devices such as a keyboard, a mouse, a touch panel, and various switches. The input unit 150 outputs, to the control unit 120, an input signal that depends on operation input from the outside.

The display unit 160 includes a display device such as a liquid crystal display (LCD), an electro luminescence (EL) display, and a cathode ray tube (CRT) display. The display unit 160 displays various screens based on display signals output from the control unit 120.

Figure 3:
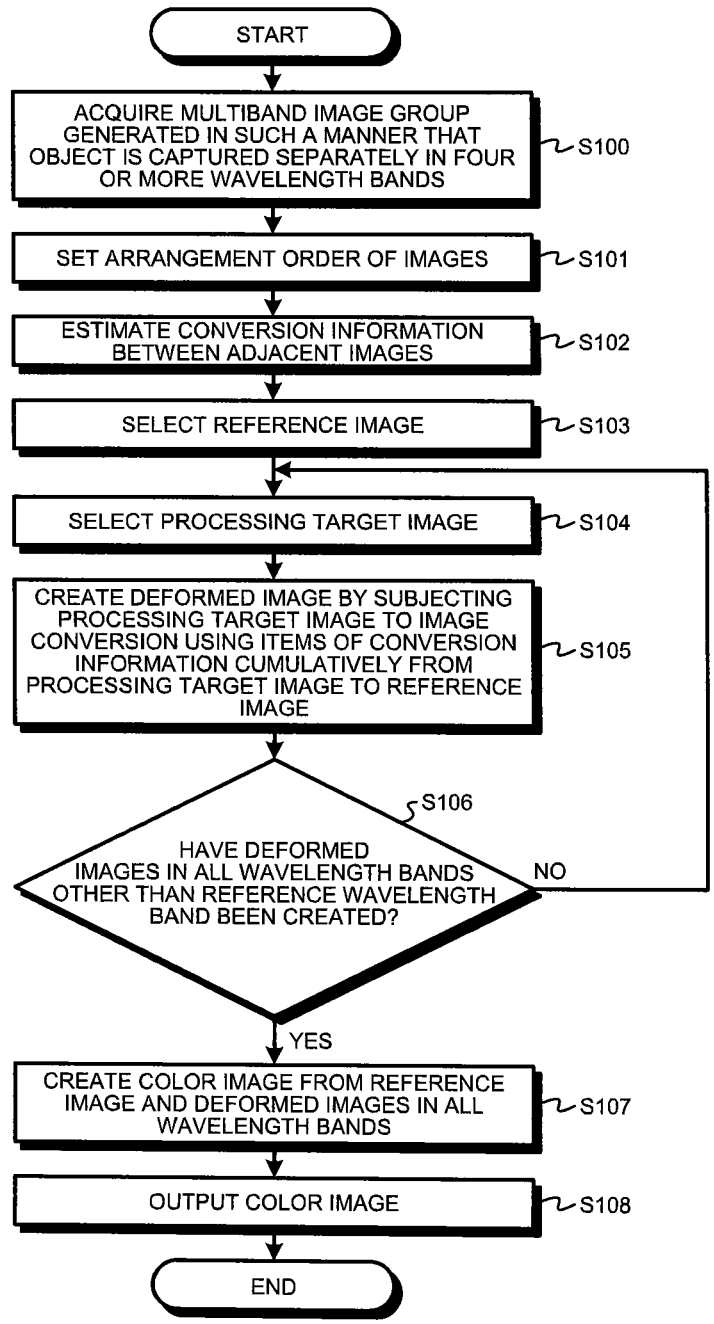
FIG. 3 is a flowchart illustrating operation of the imaging system illustrated in FIG. 1.
Figure 4:
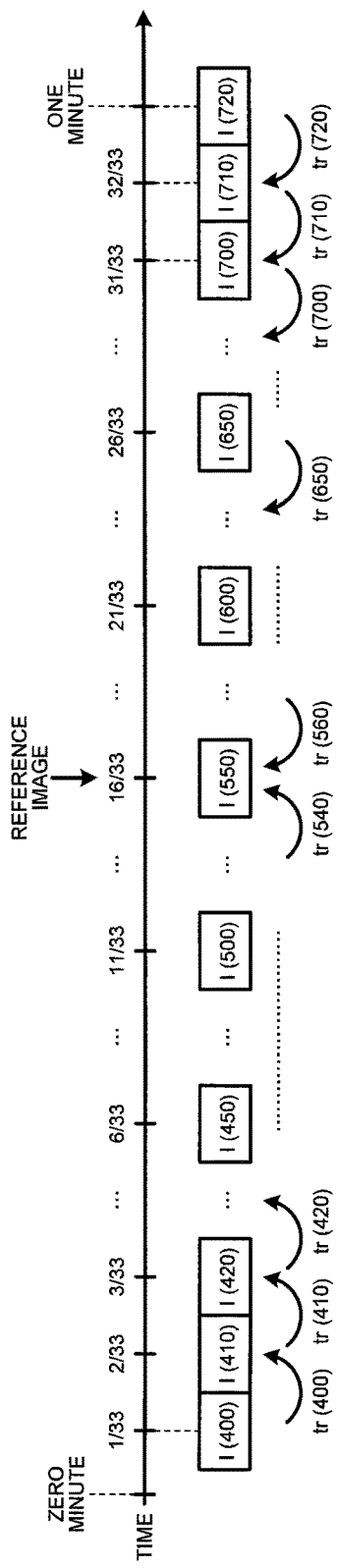
FIG. 4 is a schematic diagram for explaining the operation of the imaging system illustrated in FIG. 1.

Next, the operation of the imaging system 1 will be described. FIG. 3 is a flowchart illustrating the operation of the imaging system 1. FIG. 4 is a schematic diagram for explaining the operation of the imaging system 1.

First, in step S100, the calculation unit 140 acquires the multiband image group generated in such a manner that the object is captured separately in the four or more wavelength bands. More specifically, the imaging device 10 is operated under the frame sequential multiband imaging controller 121, and images are sequentially captured at a capturing period of 1/33 minutes, that is, at a capturing frame rate of 33 frames per minute, while the center wavelength of the wavelength band is shifted by 10 nm between 400 nm to 720 nm (refer to FIG. 4). The image acquisition unit 110 sequentially acquires, from the imaging device 10, pieces of image data of the images in the 33 bands generated in this manner, and causes the image data storage unit 132 to store the pieces of image data. The calculation unit 140 reads the pieces of image data from the image data storage unit 132 to acquire the multiband image group. Hereinafter, an image in the wavelength band having a center wavelength of $\lambda$ is described as an image $I(\lambda)$.

In subsequent step S101, the calculation unit 140 sets the arrangement order of the images in the multiband image group. More specifically, in a case where a still image display is performed in the image processing device 100, the arrangement order setting unit 141 sets the arrangement order so that the wavelength bands are adjacent to each other between the adjacent images. In the case of FIG. 4, since the wavelength band is sequentially shifted from a short wavelength side to a long wavelength side, the arrangement order of the images only needs to be set in accordance with capturing order.

In subsequent step S102, the conversion information estimation unit 144 performs conversion estimation on the two images adjacent to each other in the arrangement order set in step S101, thereby estimating the conversion information (conversion parameter) between these images. As used herein, the conversion estimation is a process of estimating the items of conversion information that coincide when the two images are caused to overlap each other. An example of the conversion estimation includes, as disclosed in JP 2007-257287 A, a process of acquiring accurate conversion information by repeating the estimation of the conversion information such as the plane projection conversion that is based on concentration gradient information. Examples of the conversion process to be estimated include a well-known image conversion such as the non-rigid conversion, the plane projection conversion, the affine conversion, the linear conversion, the scale conversion, the rotation conversion, and the translation, or combinations of them.

The conversion information estimation unit 144 executes the above-mentioned conversion estimation on all the combinations of the adjacent two images included in the multiband image group. For example, in the case of FIG. 4, conversion information tr(400) between an image I(400) and an image I(410), conversion information tr(410) between the image I(410) and an image I(420), etc. are estimated.

In subsequent step S103, the reference image selector 142 selects any one image included in the multiband image group as the reference image. In FIG. 4, for example, an image I(550) in the wavelength band having a center wavelength of 550 nm is regarded as the reference image. Hereinafter, the wavelength band of the reference image is also referred to as a reference wavelength band.

In subsequent step S104, the processing target image selector 143 selects the processing target image from among the images included in the multiband image group other than the reference image.

In subsequent step S105, the deformed image creation unit 145 creates the deformed image by subjecting the processing target image to the image conversion using the items of conversion information cumulatively from the processing target image to the reference image. For example, in FIG. 4, in a case where the image I(410) is the processing target image, items of conversion information about the image I(420) to an image I(540) located between the image I(410) and the image I(550) serving as the reference image are utilized. More specifically, total conversion information (cumulative conversion information) is calculated in such a manner that the conversion information tr(410) between the image I(410) and the image I(420), conversion information tr(420) between the image I(420) and an image I(430), . . . , and conversion information tr(540) between the image I(540) and the image I(550) are sequentially cumulated, and the image I(410) is subjected to the image conversion using the cumulative conversion information.

In this case, order in which the items of conversion information are utilized is order from the processing target image to the reference image. More specifically, in a case where the wavelength band of the processing target image is a shorter wavelength band than the reference wavelength band, that is, particularly in a case where the images I(400) to I(540) are the processing target images in FIG. 4, the items of conversion information are utilized cumulatively from the short wavelength side to the long wavelength side. On the other hand, in a case where the wavelength band of the processing target image is a longer wavelength band than the reference wavelength band, that is, particularly in a case where images I(560) to I(720) are the processing target images in FIG. 4, the items of conversion information are utilized cumulatively from the short wavelength side to the long wavelength side. For example, in a case where an image I(650) is regarded as the processing target image, first, total conversion information (cumulative conversion information) is calculated in such a manner that conversion information tr(650) between the image I(650) and an image I(640), conversion information tr(640) between the image I(640) and an image I(630), . . . , and conversion information tr(560) between the image I(560) and the image I(550) are sequentially cumulated, and the image I(650) is subjected to the image conversion using the cumulative conversion information.

In step S106, the deformed image creation unit 145 determines whether the deformed images of the images in all the wavelength bands other than the reference wavelength band have been created. In a case where the wavelength band other than the reference wavelength band for which the deformed image has not been created remains (step S106: No), the operation of the calculation unit 140 returns to step S104.

On the other hand, in a case where the deformed images in all the wavelength bands other than the reference wavelength band have been created (step S106: Yes), the color image creation unit 146 then creates the color image from the reference image and the deformed images in all the wavelength bands (step S107). More specifically, the color image creation unit 146 creates the color image by correcting each of the deformed images using a spectral characteristic of illumination, and multiplying the corrected deformed image by a spectral characteristic of rendering illumination, a color matching function, and an sRGB conversion matrix.

In subsequent step S108, the calculation unit 140 outputs the color image created in step S107. Accordingly, the control unit 120 causes the display unit 160 to display the color image, and causes the image data storage unit 132 to store the image data of the color image.

After that, the operation of the imaging system 1 is finished.

As described above, according to the first embodiment of the present disclosure, even in a case where a correlation between the reference wavelength band and the wavelength band of the processing target image is low, the items of conversion information are used cumulatively from the processing target image to the reference image, whereby the processing target image is deformed. Therefore, the processing target image can be suitably corrected with respect to the reference image without the need for complicated processes. Thus, it is possible to generate the color image in which the color deviation caused by the chromatic aberration is reduced.

In the above-mentioned first embodiment, when the multiband imaging is performed, the wavelength band is monotonically shifted from the short wavelength side to the long wavelength side. Alternatively, the wavelength band may be monotonically shifted from the long wavelength side to the short wavelength side, or may be shifted at random. In any of these cases, in a case where a still image is displayed, the arrangement order setting unit 141 sets the arrangement order of the images in the multiband image group. Therefore, order of the wavelength bands at the time of performing the multiband imaging does not need to be particularly considered.

In addition, in the above-mentioned first embodiment, the arrangement order of the images in the multiband image group is uniformly set, and the items of conversion information are used in order along the arrangement order for all the processing target images, whereby the deformed images are created. Alternatively, the arrangement order may be varied in accordance with the processing target image.

First Variation

Figure 5:
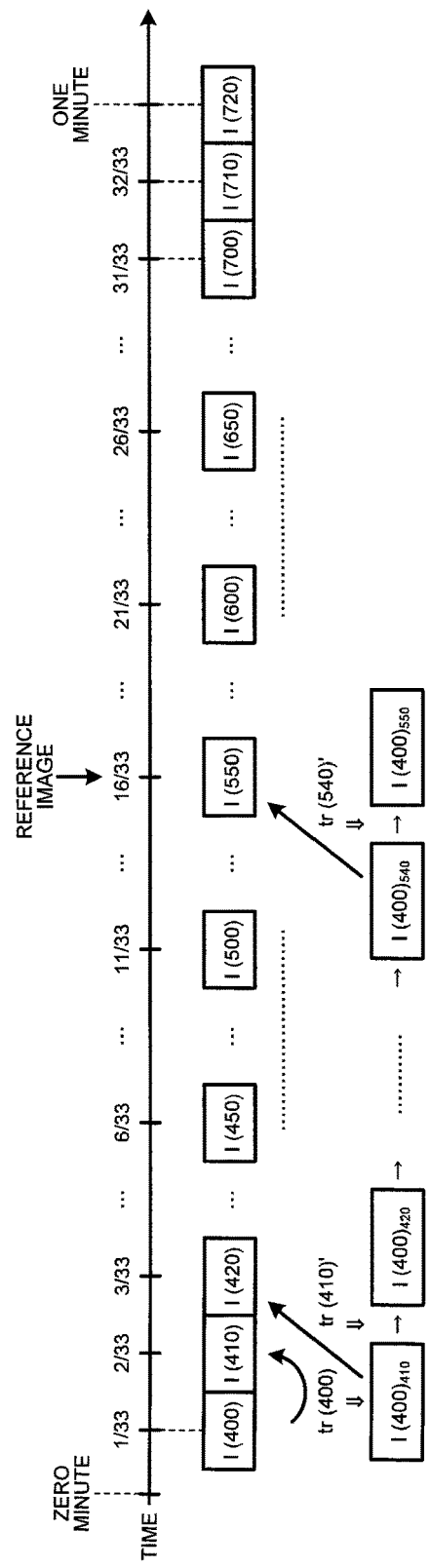
FIG. 5 is a schematic diagram for explaining operation of an imaging system according to a first variation of the first embodiment of the present disclosure.

Next, a first variation of the first embodiment of the present disclosure will be described. FIG. 5 is a schematic diagram for explaining operation of an imaging system according to the first variation of the first embodiment of the present disclosure.

In the above-mentioned first embodiment, the items of conversion information are estimated for all the combinations of the two images adjacent to each other in the arrangement order set by the arrangement order setting unit 141 (refer to step S102 in FIG. 3), and after that, the deformed images of the respective processing target images are created using the required items of conversion information (step S105). However, the estimation of the conversion information may be performed every time the deformed image of each processing target image is created.

For example, in a case where the image I(400) is regarded as the processing target image in FIG. 5, the conversion information estimation unit 144 first estimates the conversion information tr(400) between the image I(400) and the adjacent image I(410). The deformed image creation unit 145 converts the image I(400) using the conversion information tr(400) to create a deformed image I(400)$_{410}$. Next, the conversion information estimation unit 144 estimates conversion information tr(410)' between the image I(420) that comes next in the arrangement order and the deformed image I(400)$_{410}$ created immediately before. The deformed image creation unit 145 further deforms the deformed image I(400)$_{410}$ using the conversion information tr(410)' to create a deformed image I(400)$_{420}$. In this manner, the process of estimating, along the arrangement order of the images, the conversion information between the original image and the deformed image created immediately before, and further converting the deformed image created immediately before using the conversion information is cumulatively repeated. Finally, a deformed image I(400)$_{540}$ is converted using conversion information tr(540)' between the image I(550) and the deformed image I(400)$_{540}$, whereby a final deformed image I(400)$_{550}$ of the image I(400) is acquired.

Second Embodiment

Figure 6:
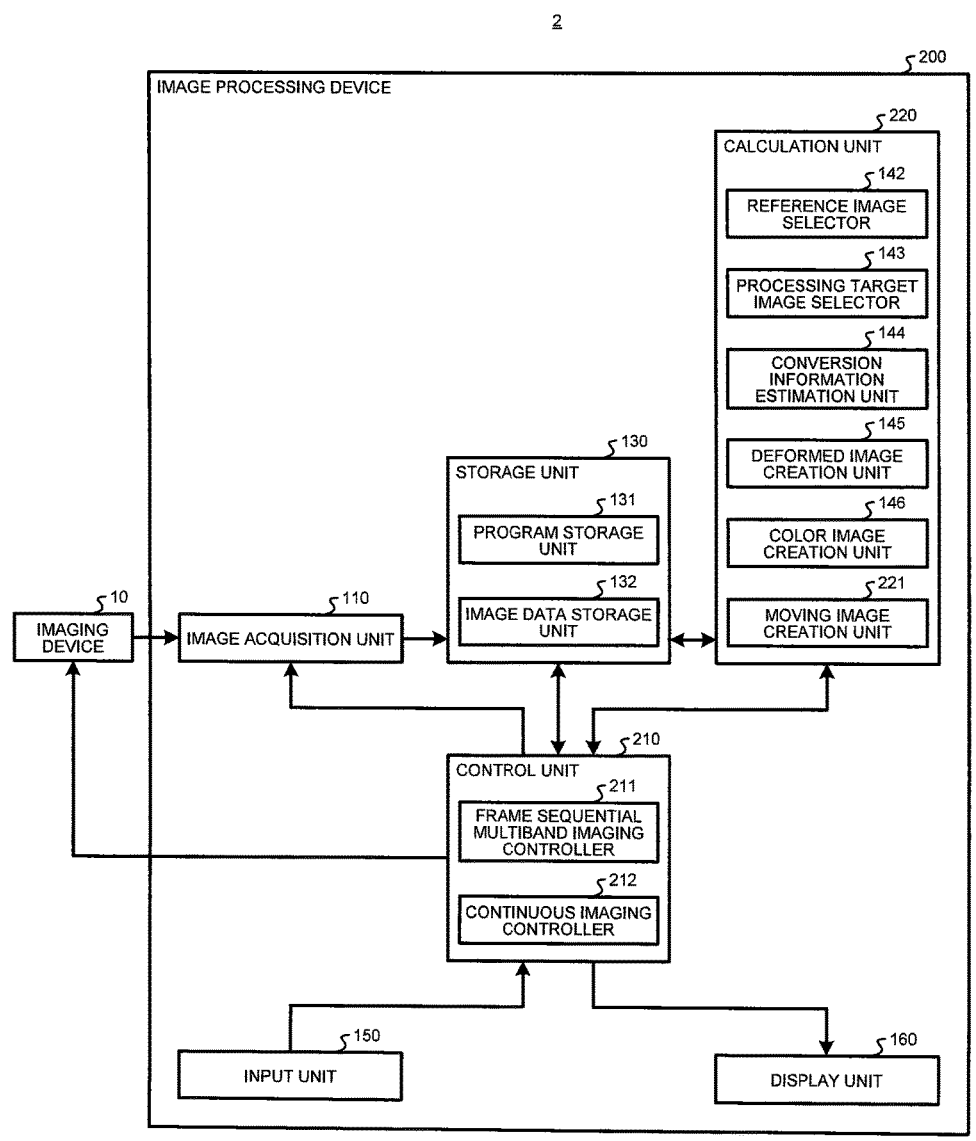
FIG. 6 is a block diagram illustrating an exemplary configuration of an imaging system according to a second embodiment of the present disclosure.

Next, a second embodiment of the present disclosure will be described. FIG. 6 is a block diagram illustrating a configuration of an imaging system according to the second embodiment of the present disclosure. As illustrated in FIG. 6, the imaging system 2 according to the second embodiment includes the imaging device 10 and an image processing device 200. The configuration and the operation of the imaging device 10 are similar to those of the first embodiment.

The image processing device 200 includes a control unit 210 and a calculation unit 220 in place of the control unit 120 and the calculation unit 140 illustrated in FIG. 1, respectively. A configuration and operation of each component of the image processing device 200 other than the control unit 210 and the calculation unit 220 are similar to those of the first embodiment.

The control unit 210 includes a frame sequential multiband imaging controller 211 and a continuous imaging controller 212. The frame sequential multiband imaging controller 211 controls the multiband imaging operation with the use of the frame sequential method in the imaging device 10. The continuous imaging controller 212 causes the imaging device 10 to continuously and repeatedly execute the operation of the multiband imaging.

The calculation unit 220 further includes a moving image creation unit 221 in addition to the reference image selector 142 to the color image creation unit 146 illustrated in FIG. 1. The moving image creation unit 221 creates a moving image using the color images sequentially created based on the pieces of image data continuously input from the imaging device 10. As used herein, the moving image may be a moving image in a standard format such as moving picture experts group (MPEG) and audio video interleave (AVI), or may be a moving image in a format unique to the image processing device 200. The operation of each of the reference image selector 142 to the color image creation unit 146 is similar to that of the first embodiment.

Figure 7:
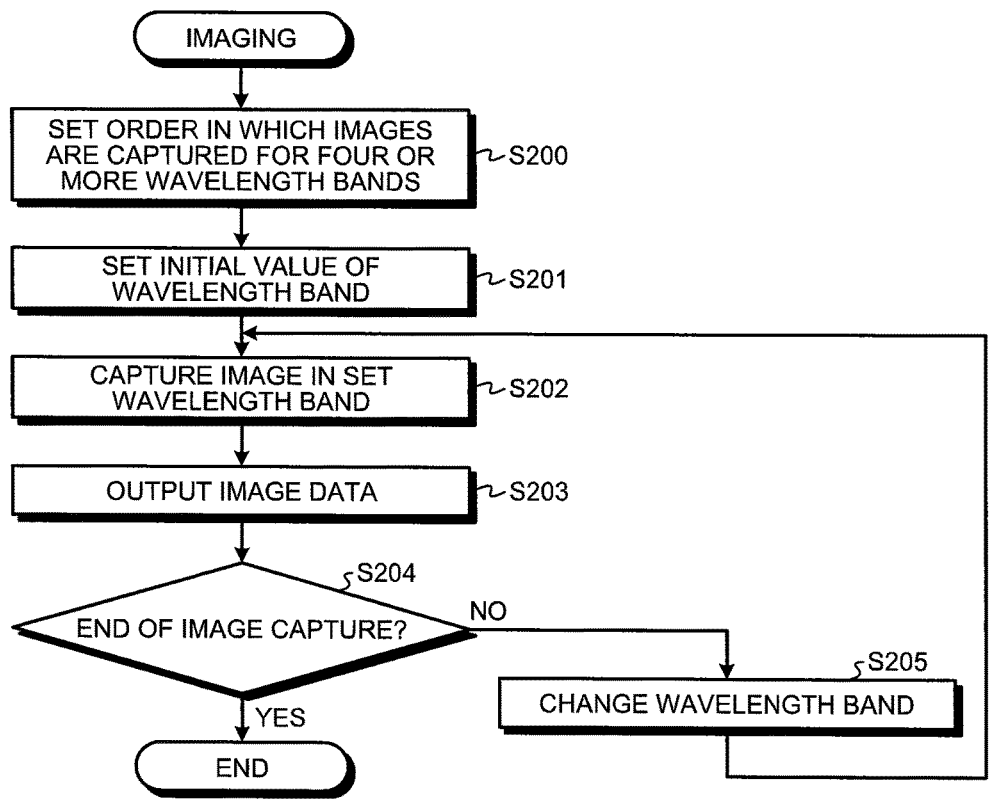
FIG. 7 is a flowchart illustrating imaging operation in the imaging system illustrated in FIG. 6.
Figure 8:
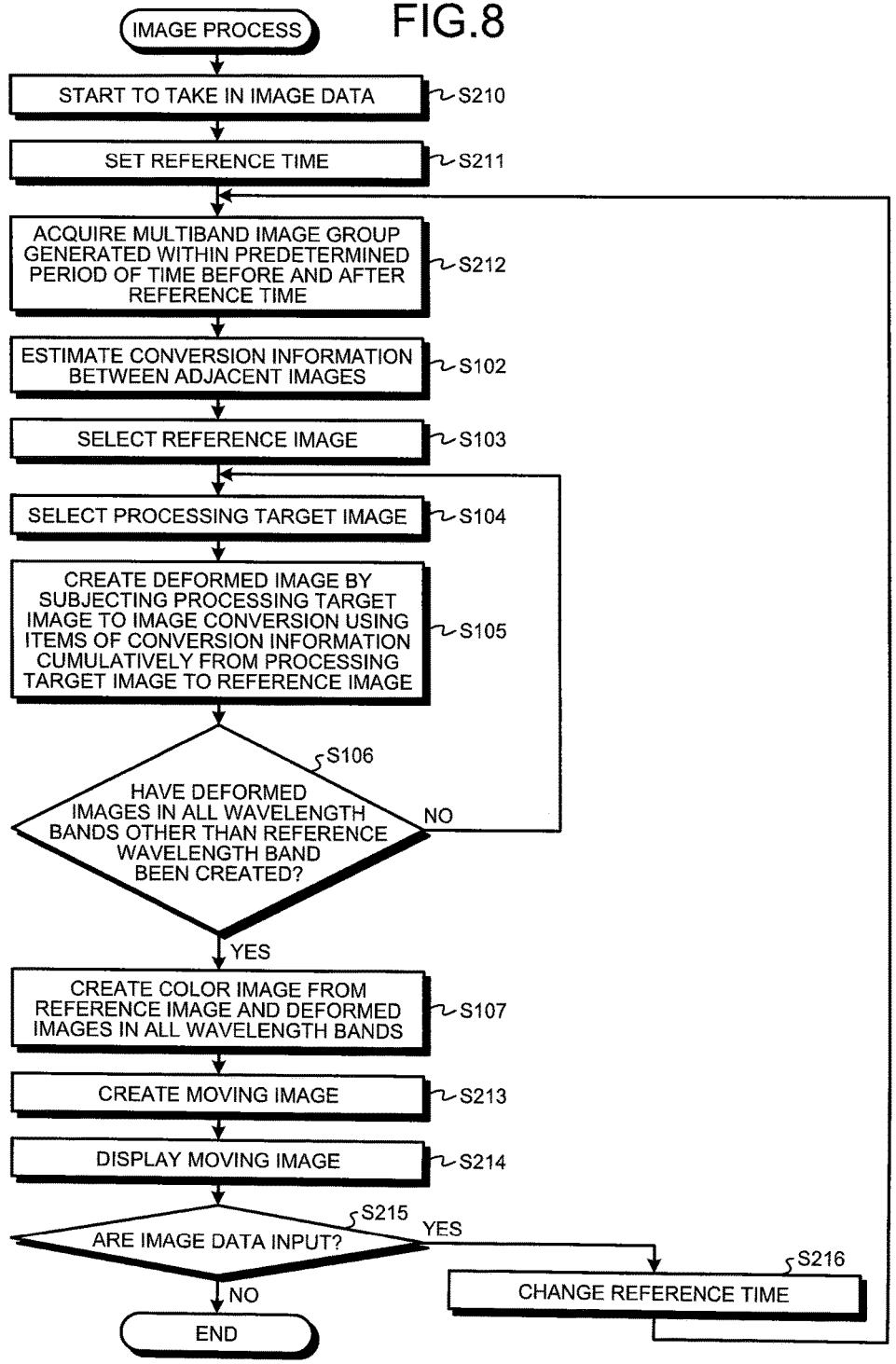
FIG. 8 is a flowchart illustrating an image process in the imaging system illustrated in FIG. 6.
Figure 9:
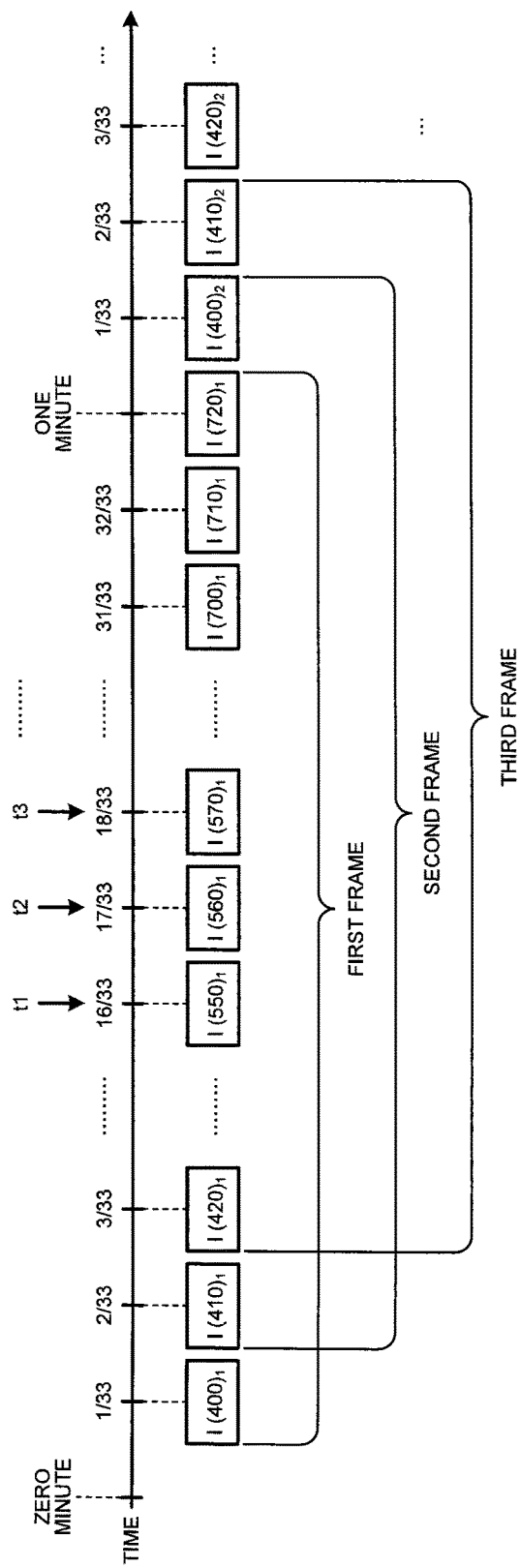
FIG. 9 is a schematic diagram for explaining operation of the imaging system illustrated in FIG. 6.

Next, operation of the imaging system 2 will be described. FIG. 7 is a flowchart illustrating imaging operation in the imaging system 2. FIG. 8 is a flowchart illustrating an image process in the imaging system 2. FIG. 9 is a schematic diagram for explaining the operation of the imaging system 2.

First, in step S200, the frame sequential multiband imaging controller 211 sets order in which images are captured for the four or more wavelength bands. In the second embodiment, the order of the wavelength bands is set so that the wavelength bands are adjacent to each other between the continuously captured images. More specifically, as illustrated in FIG. 9, the center wavelength of the wavelength band is shifted by 10 nm from the shortest wavelength of 400 nm to the longest wavelength of 720 nm.

In subsequent step S201, the frame sequential multiband imaging controller 211 sets an initial value of the wavelength band at the time of starting the multiband imaging. In the second embodiment, as illustrated in FIG. 9, the multiband imaging is started from the wavelength band having a center wavelength of 400 nm.

In step S202, the imaging device 10 captures the object in the wavelength band set in step S201, and generates the image data. In subsequent step S203, the imaging device 10 outputs the generated image data to the image processing device 200.

In step S204, the imaging device 10 determines whether a control signal for the end of the image capture has been input from the continuous imaging controller 212. In a case where the control signal for the end of the image capture has not been input (step S204: No), the imaging device 10 changes the wavelength band in the order set in step S200 (step S205). After that, the operation of the imaging device 10 proceeds to step S202. The above-mentioned operation is repeated, whereby the pieces of image data of the images in the respective wavelength bands are sequentially output to the image processing device 200. In a case where the wavelength band reaches the longest wavelength of 720 nm, the wavelength band returns to the shortest wavelength of 400 nm, and the wavelength band is shifted again from the short wavelength side to the long wavelength side.

On the other hand, in a case where the control signal for the end of the image capture has been input from the continuous imaging controller 212 (step S204: Yes), the imaging operation of the imaging device 10 is finished.

In response to the pieces of image data output from the imaging device 10 (refer to step S203 in FIG. 7), the image processing device 200 starts to take in the pieces of image data, and causes the image data storage unit 132 to sequentially store the pieces of image data (refer to step S210 in FIG. 8).

In subsequent step S211, the calculation unit 220 sets an arbitrary reference time. In FIG. 9, first, a time t1 is set as the reference time.

In step S212, the calculation unit 220 acquires, in capturing time order, the multiband image group generated within a predetermined period of time before and after the reference time based on the pieces of image data sequentially stored in the image data storage unit 132. The image group may be acquired in any range as long as all the wavelength bands are covered, and there may be some redundant wavelength bands. For example, as illustrated in FIG. 9, in a case where the images in all the 33 bands are generated during one minute, images generated during at least one minute including the reference time only need to be acquired. In FIG. 9, images I(400)$_1$ to I(720)$_1$ generated during 30 seconds before and after the time t1 serving as the center are acquired. The reference time does not necessarily need to be located in the center of the period during which the images are acquired.

Operation of each of steps S102 to S107 subsequent to step S212 is similar to that of the first embodiment. Among them, in step S102, the conversion information between the images arranged in the capturing time order is estimated. In step S103, an image at the reference time set in step S211 (in FIG. 9, an image I(550) corresponding to the time t1) is set as the reference image. Consequently, the color image is created based on the images I(400)$_1$ to I(720)$_1$ (refer to step S107).

In step S213 subsequent to step S107, the moving image creation unit 221 creates the moving image using the color image created in step S107 as a frame image at the reference time. For example, the color image created based on the images I(400)$_1$ to I(720)$_1$ becomes an image for a first frame corresponding to the reference time t1.

Accordingly, the calculation unit 220 outputs the created moving image, and the control unit 210 causes the display unit 160 to display the moving image with the use of the color image (step S214).

In step S215, in a case where a new piece of image data is input from the imaging device 10 (step S215: Yes), the calculation unit 220 changes the reference time (step S216). Although any period of the reference time can be employed, it is better to shorten the period of the reference time in order to create the moving image at a high frame rate. For example, in FIG. 9, subsequent to the time t1, a time t2 after $\frac{1}{33}$ minutes that are equal to the capturing period is set as the reference time. After that, the operation of the calculation unit 220 returns to step S212.

The above-mentioned operation is repeated, whereby the color images as the respective frame images for the moving image are sequentially created based on the multiband image groups generated within the predetermined period of time including the reference times. For example, a color image for a second frame is created based on images I(410)$_1$ to I(400)$_2$ generated during 30 seconds before and after the reference time t2, and a color image for a third frame is created based on images I(420)$_1$ to I(410)$_2$ generated during 30 seconds before and after a reference time t3.

On the other hand, in step S215, in a case where the input of the image data from the imaging device 10 has been finished (step S215: No), the operation of the image processing device 200 is finished.

As described above, according to the second embodiment of the present disclosure, the capturing order of the respective wavelength bands is set so that the wavelength bands are adjacent to each other between the continuously captured images. Therefore, the color image in which both the color deviation caused by the chromatic aberration and a blur caused by a difference in the capturing time are corrected with a good degree of accuracy can be created. Thus, the color moving image of good image quality can be created by using such color images.

In steps S213 and S214 mentioned above, the moving image is created and displayed in real time using the pieces of image data sequentially input from the imaging device 10. Alternatively, the moving image may be created in such a manner that the color images created in step S107 are stored, and the accumulated color images are connected.

Third Embodiment

Figure 10:
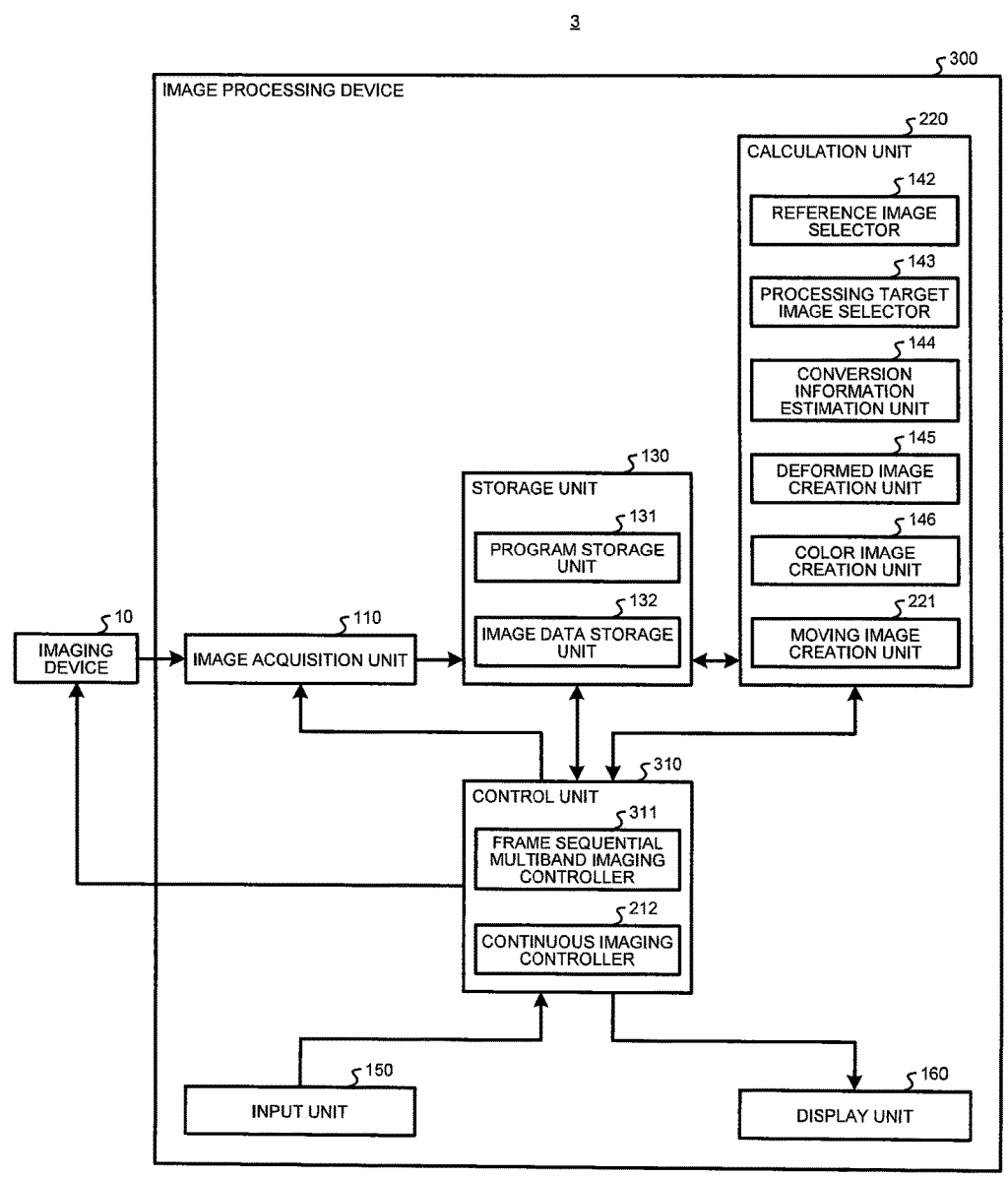
FIG. 10 is a block diagram illustrating an exemplary configuration of an imaging system according to a third embodiment of the present disclosure.

Next, a third embodiment of the present disclosure will be described. FIG. 10 is a block diagram illustrating a configuration of an imaging system according to the third embodiment of the present disclosure. As illustrated in FIG. 10, the imaging system 3 according to the third embodiment includes the imaging device 10 and an image processing device 300. The image processing device 300 includes a control unit 310 in place of the control unit 210 illustrated in FIG. 6. The configuration and the operation of the imaging device 10 are similar to those of the first embodiment. A configuration and operation of the image processing device 300 other than the control unit 310 are similar to those of the second embodiment.

The control unit 310 includes a frame sequential multiband imaging controller 311 and the continuous imaging controller 212. The frame sequential multiband imaging controller 311 controls the multiband imaging operation with the use of the frame sequential method in the imaging device 10. The continuous imaging controller 212 causes the imaging device 10 to continuously and repeatedly execute the multiband imaging operation. The frame sequential multiband imaging controller 311 controls change operation for the wavelength band and controls a direction in which the wavelength band is changed when causing the imaging device 10 to execute the multiband imaging. The operation of the continuous imaging controller 212 is similar to that of the second embodiment.

Figure 11:
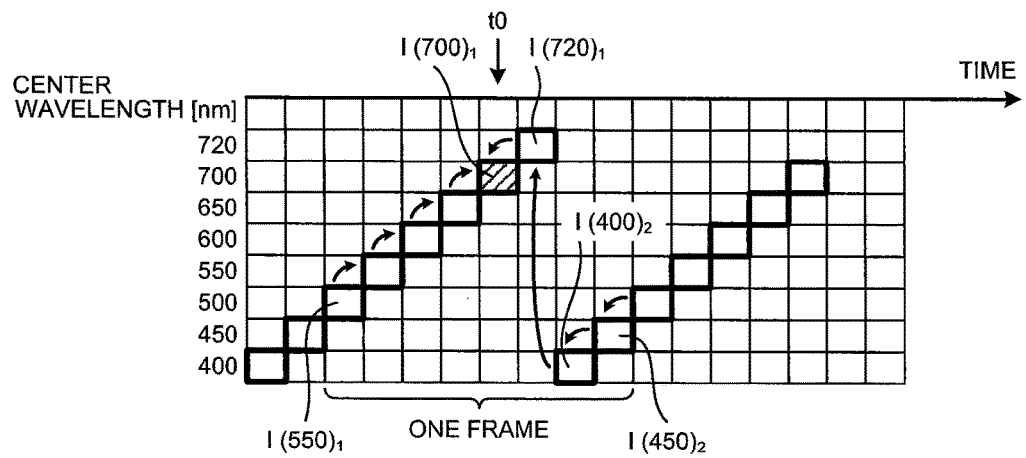
FIG. 11 is a schematic diagram for explaining operation of the imaging system illustrated in FIG. 10.

As in the second embodiment, in a case where the wavelength band is monotonically shifted from the short wavelength side to the long wavelength side, a timing at which the wavelength band jumps from the longest wavelength to the shortest wavelength is sometimes included in the period of time during which the multiband image group is acquired based on the reference time. More specifically, as illustrated in FIG. 11, in a case where the multiband imaging is performed in eight bands having center wavelengths of 400 nm to 720 nm, images I(550)$_1$ to I(450)$_2$ are acquired as the multiband image group with respect to a reference time t0. In this multiband image group, since the image I(720)$_1$ and the image I(400)$_2$ having a low correlation between the wavelength bands come in succession, conversion estimation accuracy between both the images is reduced. Therefore, accuracy of the deformed image created by utilizing the conversion information between the image I(720)$_1$ and the image I(400)$_2$ is deteriorated. For example, in the case of FIG. 11, the accuracy of a deformed image created from the image I(450)$_2$ to a reference image I(700)$_1$ or a deformed image created from the I(400)$_2$ to the reference image I(700)$_1$ is deteriorated. As a result, it might be difficult to create an appropriate color image.

Figure 12:
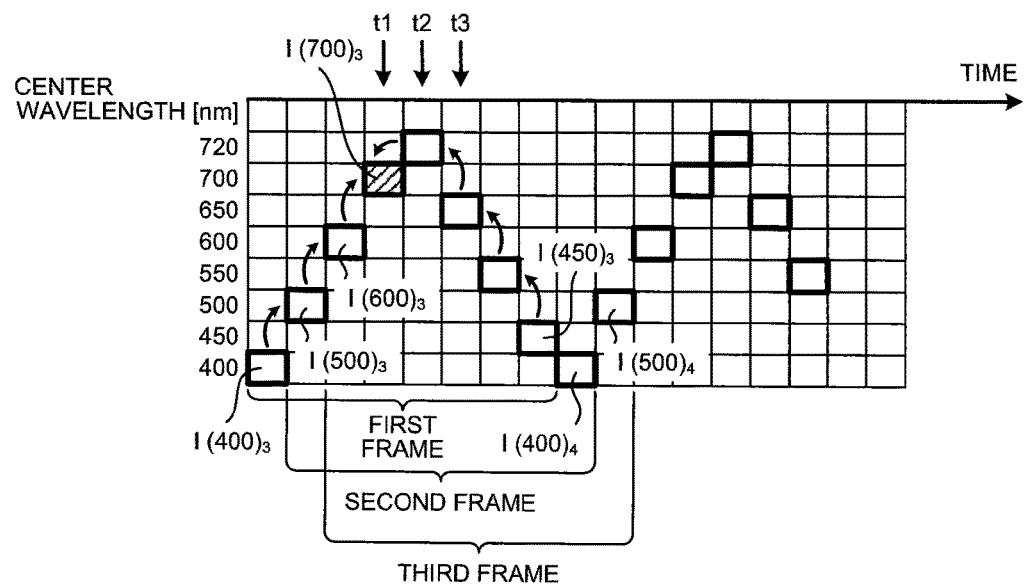
FIG. 12 is a schematic diagram for explaining the operation of the imaging system illustrated in FIG. 10.

In this regard, in the third embodiment, as illustrated in FIG. 12, the wavelength band is shifted at intervals of one or more levels when the images are continuously captured, and the wavelength band is caused to reciprocate at least once between the shortest wavelength band and the longest wavelength band during one cycle of the multiband imaging, so that the shortest wavelength band and the longest wavelength band are not directly adjacent to each other, that is, another wavelength band is inserted between the shortest wavelength band and the longest wavelength band. More specifically, in the case of FIG. 12, the center wavelength is first shifted in order of 400 nm, 500 nm, 600 nm, and 700 nm. Then, images in the respective wavelength bands are acquired, and an image in the longest wavelength band is acquired. In other words, in a forward path, the wavelength bands having center wavelengths of 450 nm, 550 nm, and 650 nm are skipped. After that, the center wavelength is shifted in order of 650 nm, 550 nm, and 450 nm, and images in the respective wavelength bands are acquired. In other words, in a return path, the wavelength bands having center wavelengths of 700 nm, 600 nm, and 500 nm are skipped.

During the one cycle of the multiband imaging, images in the same wavelength band may be redundantly captured. In this case, in terms of efficiency of the image process in the image processing device 300, the number of times of capturing the redundant images is preferably a half or less of the number of times of capturing the images during the one cycle.

In a case where the multiband imaging is performed while the wavelength band is shifted in such a cycle, the correlation between the wavelength bands can be maintained at a high level in all the combinations of the images in the multiband image group adjacent to each other in the capturing order, regardless of the set reference time. More specifically, in any of a multiband image group $I(400)_3$ to $I(450)_3$ extracted based on the reference time t1, a multiband image group $I(500)_3$ to $I(400)_4$ extracted based on the reference time t2, and a multiband image group $I(600)_3$ to $I(500)_4$ extracted based on the reference time t3, a combination of images having a significantly low correlation between the wavelength bands does not occur between the images adjacent to each other in the capturing order.

In this manner, the frame sequential multiband imaging controller 311 causes the imaging device 10 to shift the wavelength band at intervals of one or more levels every time a single image is captured. Consequently, the frame sequential multiband imaging controller 311 performs control to cause the wavelength band to reciprocate at least once between the shortest wavelength band and the longest wavelength band during the one cycle of the multiband imaging.

Figure 13:
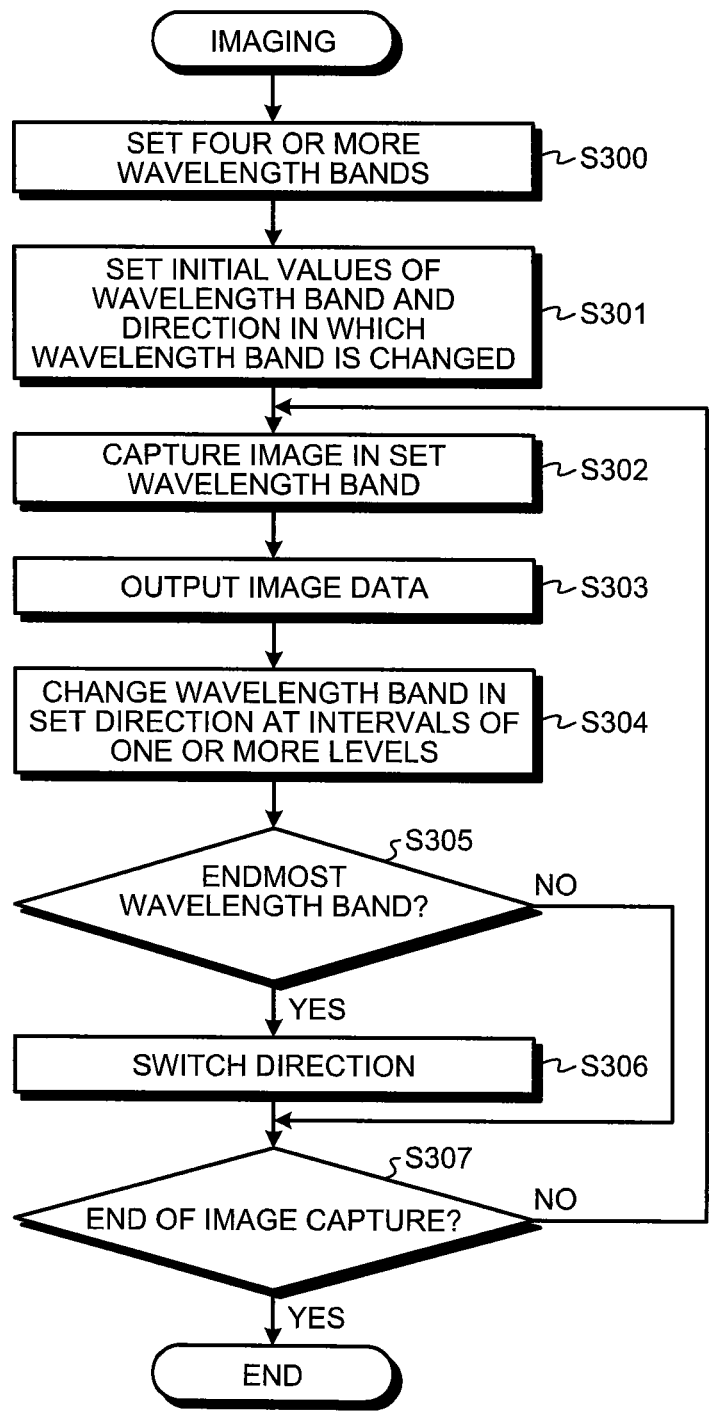
FIG. 13 is a flowchart illustrating imaging operation in the imaging system illustrated in FIG. 10.

FIG. 13 is a flowchart illustrating imaging operation in the imaging system 3. First, in step S300, the frame sequential multiband imaging controller 311 sets the four or more wavelength bands in which the multiband imaging is performed. In the third embodiment, as illustrated in FIG. 11, the multiband imaging is performed in the eight wavelength bands having center wavelengths of 400 nm to 720 nm.

In subsequent step S301, the frame sequential multiband imaging controller 311 sets initial values of the wavelength band and the direction in which the wavelength band is changed. In the third embodiment, the shortest wavelength band having a center wavelength of 400 nm is set as the initial value of the wavelength band, and ascending order is set as the initial value of the direction in which the wavelength band is changed.

In step S302, the imaging device 10 captures the object in the wavelength band set in step S301, and generates the image data. In subsequent step S303, the imaging device 10 outputs the generated image data to the image processing device 300.

In step S304, the imaging device 10 changes the wavelength band in the direction set in step S301 at intervals of one or more levels. More specifically, the wavelength band having a center wavelength of 400 nm is changed to the wavelength band having a center wavelength of 500 nm while the wavelength band having a center wavelength of 450 nm is skipped.

In step S305, the frame sequential multiband imaging controller 311 determines whether the changed wavelength band is an endmost wavelength band of the wavelength bands set in step S300, that is, whether the changed wavelength band is an upper end wavelength band or a lower end wavelength band. In a case where the changed wavelength band is the endmost wavelength band (step S305: Yes), the frame sequential multiband imaging controller 311 switches the direction in which the wavelength band is changed (step S306). For example, in a case where the center wavelength of the wavelength band changed in step S304 is 720 nm, that is, the upper end wavelength band, the direction in which the wavelength band is changed is switched to descending order. On the other hands, in a case where the changed wavelength band is not the endmost wavelength band (step S305: No), the operation immediately proceeds to step S307.

In step S307, the imaging device 10 determines whether a control signal for the end of the image capture has been input from the continuous imaging controller 212. In a case where the control signal for the end of the image capture has not been input (step S307: No), the operation of the imaging device 10 proceeds to step S302. In this case, an image is captured in the wavelength band changed in step S304. On the other hand, in a case where the control signal for the end of the image capture has been input (step S307: Yes), the operation of the imaging device 10 is finished.

As described above, according to the third embodiment of the present disclosure, the correlation between the wavelength bands can be maintained at a high level in all the combinations of the images in the multiband image group adjacent to each other in the capturing order, regardless of the setting of the reference time. Consequently, a reduction in the correlation between the local wavelength bands can be prevented. Therefore, the color image in which both the color deviation caused by the chromatic aberration and the blur caused by the difference in the capturing time are corrected with a good degree of accuracy can always be created. Thus, the color moving image of high quality can be created by using such color images.

In the imaging device, in a case where the wavelength band is varied by electric control using a liquid crystal tunable filter or the like, a control program only needs to be created so that the center wavelength of the wavelength band is varied during the one cycle, for example, in order of 400 nm, 500 nm, 600 nm, 700 nm, 720 nm, 650 nm, 550 nm, and 450 nm.

Fourth Embodiment

Figure 14:
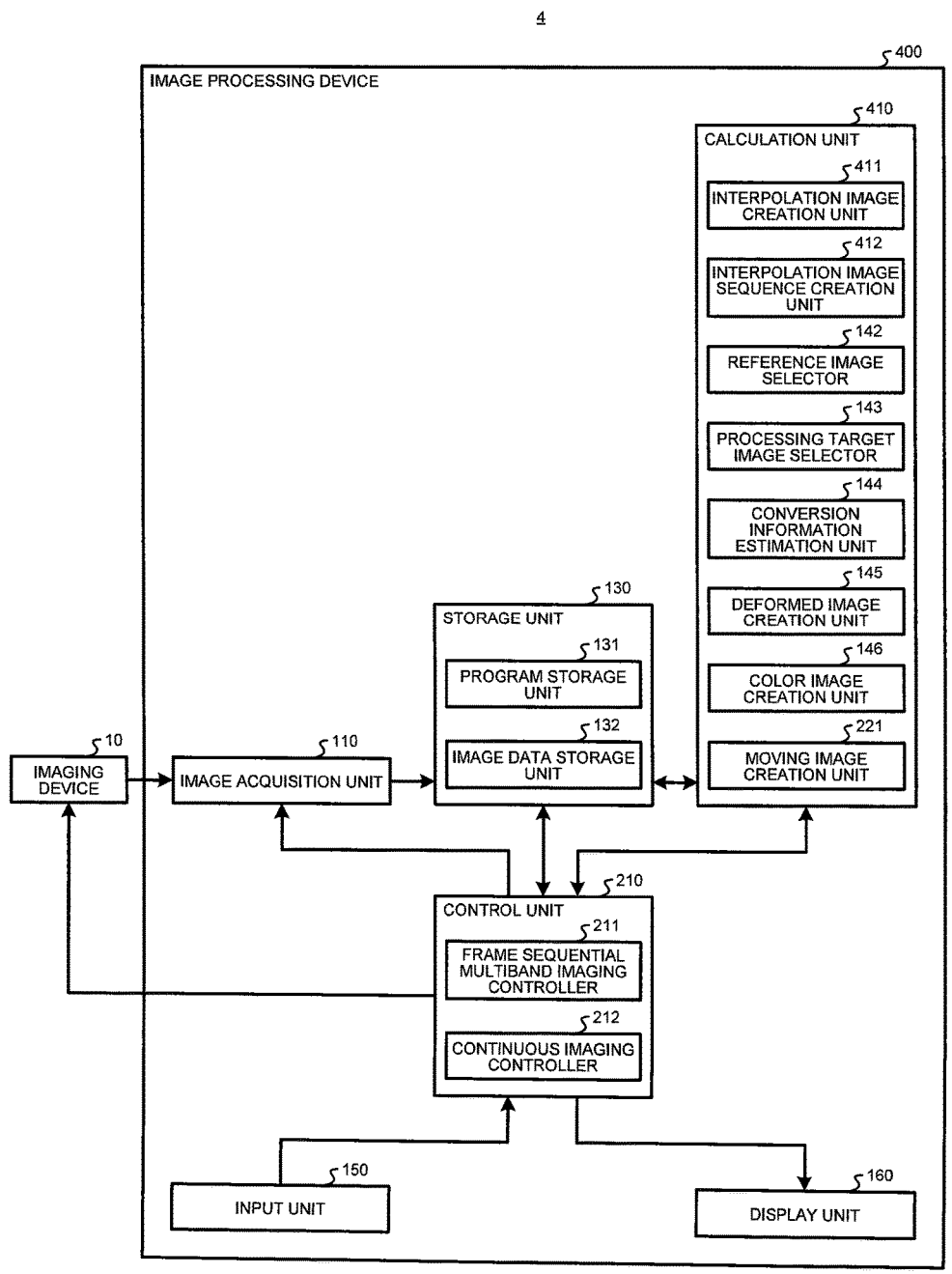
FIG. 14 is a block diagram illustrating an exemplary configuration of an imaging system according to a fourth embodiment of the present disclosure.

Next, a fourth embodiment of the present disclosure will be described. FIG. 14 is a block diagram illustrating a configuration of an imaging system according to the fourth embodiment of the present disclosure. As illustrated in FIG. 14, the imaging system 4 according to the fourth embodiment includes the imaging device 10 and an image processing device 400. The configuration and the operation of the imaging device 10 are similar to those of the first embodiment.

The image processing device 400 includes a calculation unit 410 in place of the calculation unit 220 illustrated in FIG. 6. The calculation unit 410 includes an interpolation image creation unit 411 and an interpolation image sequence creation unit 412 in addition to the configuration of the calculation unit 220 illustrated in FIG. 6. A configuration and operation of the image processing device 400 other than the calculation unit 410 are similar to those of the second embodiment.

The interpolation image creation unit 411 creates an interpolation image at the reference time from images in the same wavelength band generated before and after the reference time.

The interpolation image sequence creation unit 412 arranges the interpolation images in the respective wavelength bands generated by the interpolation image creation unit 411 in predetermined arrangement order.

Figure 15:
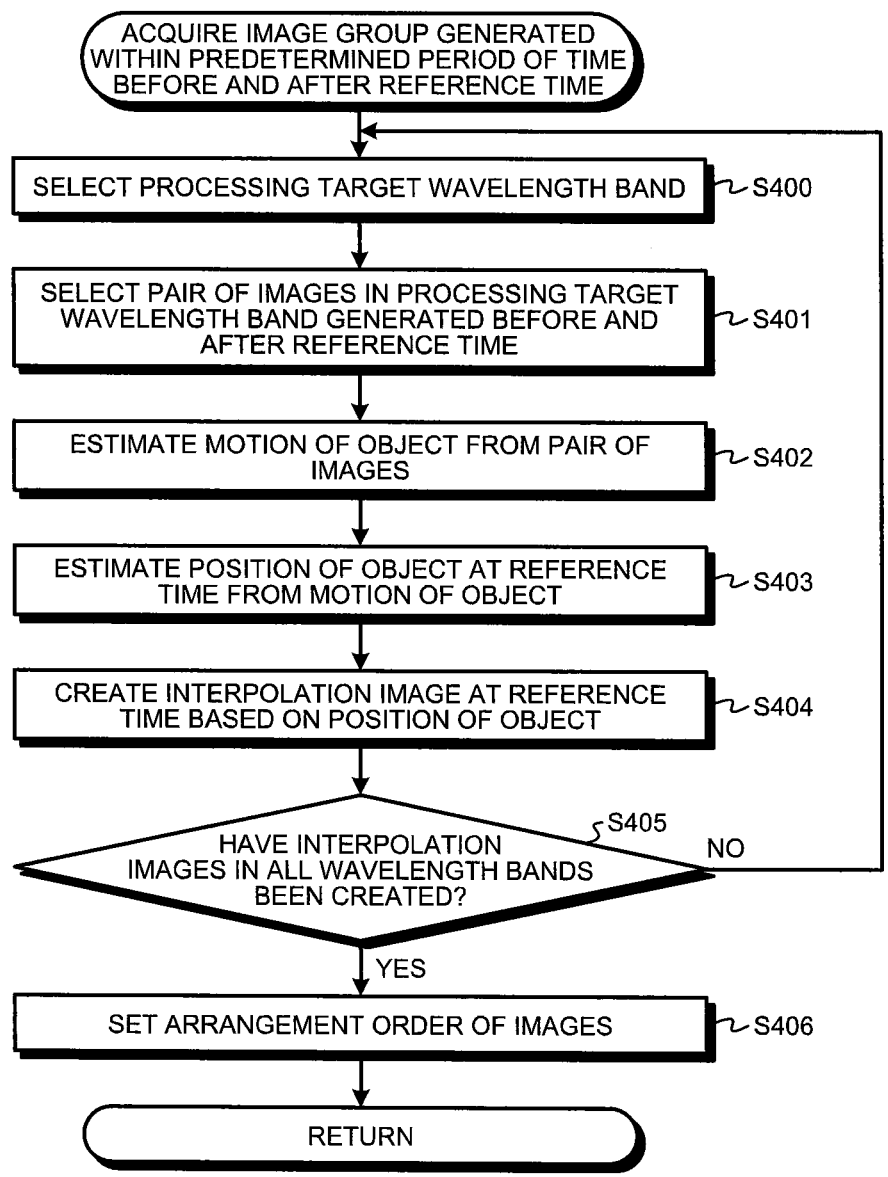
FIG. 15 is a flowchart illustrating a process of acquiring an image group that is executed by an image processing device illustrated in FIG. 14.
Figure 16:
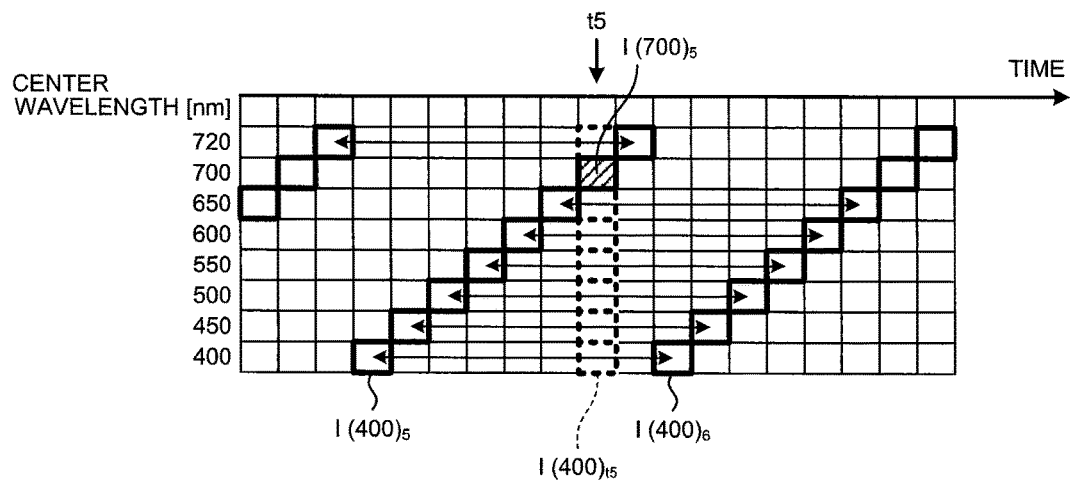
FIG. 16 is a schematic diagram for explaining an image process that is executed by the image processing device illustrated in FIG. 14.
Figure 17:
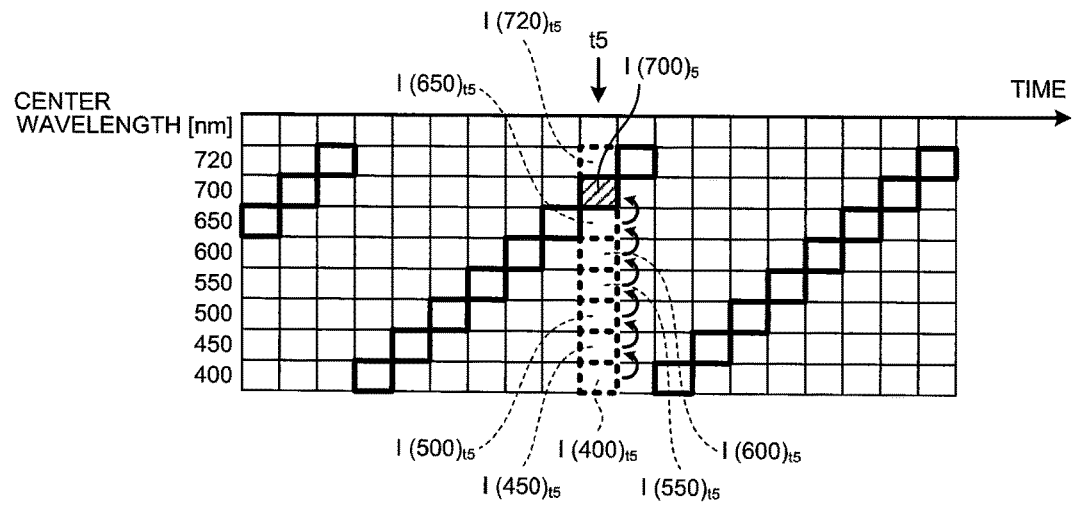
FIG. 17 is a schematic diagram for explaining the image process that is executed by the image processing device illustrated in FIG. 14.

Operation of the imaging system 4 is similar to that of the second embodiment as a whole (refer to FIGS. 7 and 8), and the operation of acquiring the image group generated within the predetermined period of time before and after the reference time in step S212 in FIG. 8 is different from that of the second embodiment. FIG. 15 is a flowchart illustrating detailed operation that is executed by the calculation unit 410 in step S212. FIGS. 16 and 17 are schematic diagrams for explaining the detailed operation of the calculation unit 410 in step S212.

First, in step S400, the interpolation image creation unit 411 selects a processing target wavelength band from among the wavelength bands other than the wavelength band at the reference time set in step S211 in FIG. 8. In subsequent step S401, the interpolation image creation unit 411 selects a pair of images in the processing target wavelength band generated before and after the reference time. For example, in FIG. 16, in a case where the center wavelength of the processing target wavelength band is 400 nm, a pair of images including an image $I(400)_5$ and an image $I(400)_6$ generated before and after a reference time t5 is selected.

In subsequent step S402, the interpolation image creation unit 411 estimates a motion of the object from the pair of images selected in step S401. A well-known technique such as a block matching method and a gradient method can be used for the estimation of the motion.

In step S403, the interpolation image creation unit 411 estimates a position of the object at the reference time from the motion of the object.

In step S404, the interpolation image creation unit 411 creates the interpolation image at the reference time based on the position of the object (for example, refer to JP 2012-142817 A). At this time, either of the pair of images used for the estimation of the motion may be used. For example, an interpolation image $I(400)_{t5}$ at the reference time t5 may be created from the image $I(400)_5$, or the interpolation image $I(400)_{t5}$ may be created from the image $I(400)_6$. Whether the image $I(400)_5$ is used or the image $I(400)_6$ is used only needs to be appropriately set in such a manner that, for example, the image at an earlier capturing time, the image at a later capturing time, or the image at a capturing time closer to the reference time is used. Alternatively, both the image $I(400)_5$ and the image $I(400)_6$ may be used to create the interpolation image $I(400)_{t5}$.

In step S405, the interpolation image creation unit 411 determines whether the interpolation images in all the wavelength bands other than the wavelength band at the reference time have been created. In a case where the wavelength band other than the wavelength band at the reference time for which the interpolation image has not been created remains (step S405: No), the operation of the calculation unit 410 proceeds to step S400. This process is repeated, whereby interpolation images $I(400)_{t5}$, $I(450)_{t5}$, $I(500)_{t5}$, $I(550)_{t5}$, $I(600)_{t5}$, $I(650)_{t5}$, and $I(720)_{t5}$ at the reference time t5 are created for the respective wavelength bands having center wavelengths of 400 nm, 450 nm, 500 nm, 550 nm, 600 nm, 650 nm, and 720 nm as illustrated in FIG. 17.

In a case where the interpolation images in all the wavelength bands other than the wavelength band at the reference time have been created (step S405: Yes), the interpolation image sequence creation unit 412 sets the arrangement order of the images so that the wavelength bands are adjacent to each other between the adjacent images for an image set including all the interpolation images and the image at the reference time (step S406). After that, the operation of the calculation unit 410 returns to the main routine.

After step S102 subsequent to step S212, the image set for which the arrangement order has been set in step S406 is regarded as the multiband image group, and the image process is executed in a manner similar to that in the second embodiment. In this case, in step S103, an image captured at the reference time is selected as the reference image. Therefore, in the case of FIG. 17, an image $I(700)_5$ is selected as the reference image, and the respective interpolation images $I(400)_{t5}$, $I(450)_{t5}$, $I(500)_{t5}$, $I(550)_{t5}$, $I(600)_{t5}$, $I(650)_{t5}$, and $I(720)_{t5}$ selected as the processing target images are converted into the deformed images by utilizing the items of conversion information estimated between the adjacent interpolation images cumulatively from the processing target images to the reference image (image $I(700)_5$) (refer to step S105).

As described above, according to the fourth embodiment of the present disclosure, the interpolation images created using the images in the respective wavelength bands generated before and after the reference time are dealt with as the multiband image group. Therefore, the color image in which both the color deviation caused by the chromatic aberration and defocus caused by the difference in the capturing time are corrected with a good degree of accuracy can be created, regardless of the order of the wavelength bands in which the images are captured. Thus, the moving image of high quality can be created by using such color images.

Fifth Embodiment

Figure 18:
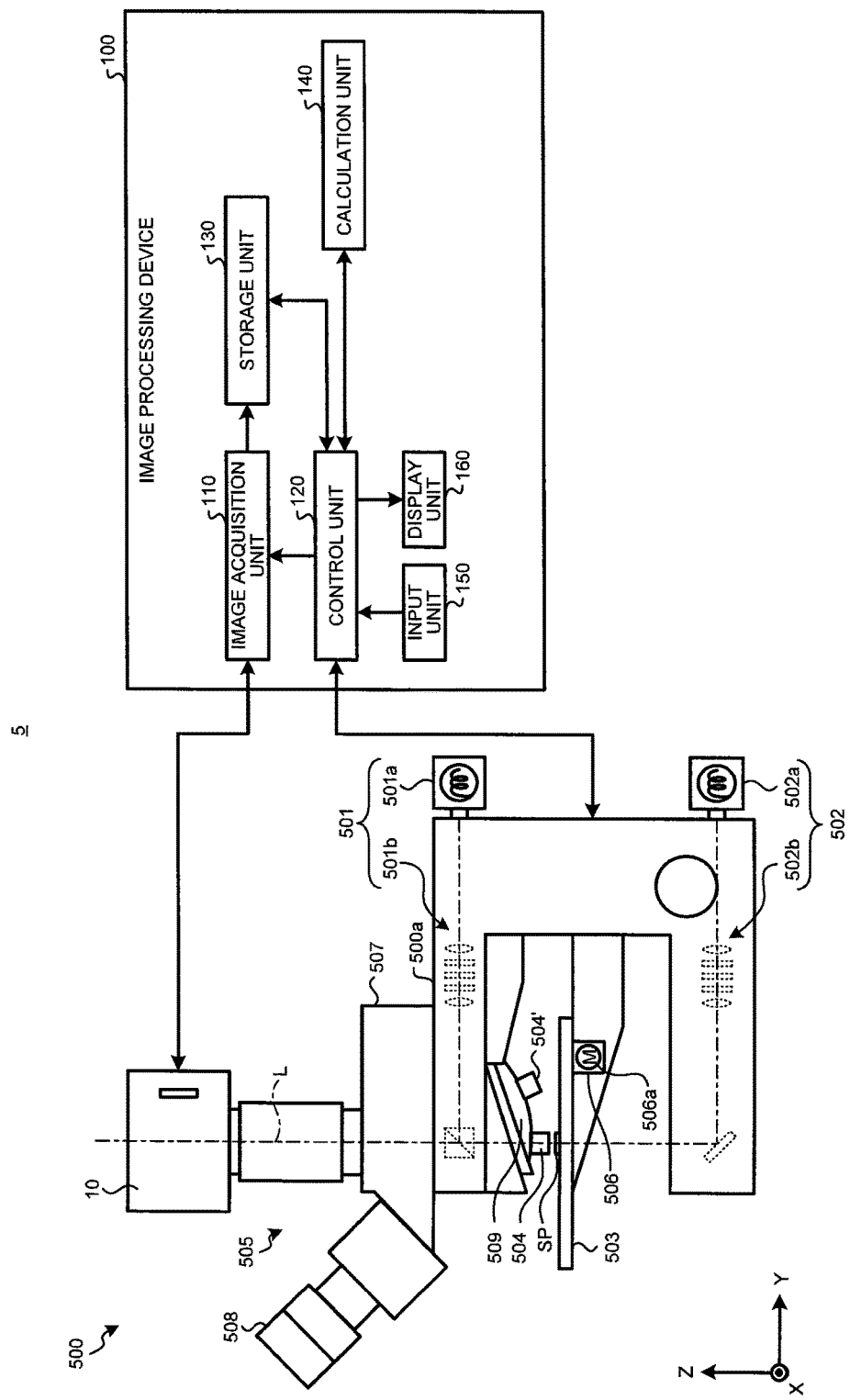
FIG. 18 is a diagram illustrating an exemplary configuration of an imaging system according to a fifth embodiment of the present disclosure.

Next, a fifth embodiment of the present disclosure will be described. FIG. 18 is a diagram illustrating an exemplary configuration of an imaging system according to the fifth embodiment of the present disclosure. As illustrated in FIG. 18, the imaging system 5 according to the fifth embodiment includes a microscope device 500 provided with the imaging device 10 and the image processing device 100. In place of the image processing device 100, the image processing device 200 illustrated in FIG. 6, the image processing device 300 illustrated in FIG. 10, or the image processing device 400 illustrated in FIG. 14 may be provided.

The microscope device 500 has a substantially C-shaped arm 500a, a specimen stage 503, an objective lens 504, and a stage position change unit 506. The arm 500a is provided with an epi-illumination unit 501 and a transmitting illumination unit 502. The specimen stage 503 is attached to the arm 500a, and an object SP to be observed is placed on the specimen stage 503. The objective lens 504 is provided at one end side of a lens barrel 505 via a trinocular lens barrel unit 507 so as to face the specimen stage 503. The stage position change unit 506 moves the specimen stage 503. The trinocular lens barrel unit 507 causes observation light of the object SP that has come in through the objective lens 504 to branch off and reach the imaging device 10 provided on the other end side of the lens barrel 505 and an eyepiece unit 508 to be described later. The eyepiece unit 508 enables a user to directly observe the object SP.

The epi-illumination unit 501 includes an epi-illumination light source 501a and an epi-illumination optical system 501b, and irradiates the object SP with epi-illumination light. The epi-illumination optical system 501b includes various optical members (a filter unit, a shutter, a field diaphragm, and an aperture diaphragm or the like) that collect illumination light emitted from the epi-illumination light source 501a and guide the illumination light in a direction of an observation light path L.

The transmitting illumination unit 502 includes a transmitting illumination light source 502a and a transmitting illumination optical system 502b, and irradiates the object SP with transmitting illumination light. The transmitting illumination optical system 502b includes various optical members (a filter unit, a shutter, a field diaphragm, and an aperture diaphragm or the like) that collect illumination light emitted from the transmitting illumination light source 502a and guide the illumination light in a direction of the observation light path L.

The objective lens 504 is attached to a revolver 509 capable of holding a plurality of objective lenses (for example, objective lenses 504 and 504') having different magnifications. This revolver 509 is rotated to change the objective lens 504, 504' that faces the specimen stage 503, whereby the imaging magnification can be varied.

A zoom unit including a plurality of zoom lenses and a drive unit that varies positions of the zoom lenses is provided inside the lens barrel 505. The zoom unit adjusts the positions of the respective zoom lenses, whereby an object image within an imaging field is magnified or reduced.

The stage position change unit 506 includes, for example, a drive unit 506a such as a stepping motor, and moves a position of the specimen stage 503 on an XY plane to vary the imaging field. The stage position change unit 506 also moves the specimen stage 503 along a Z axis, whereby the objective lens 504 is focused on the object SP.

A magnified image of the object SP generated in the above-mentioned microscope device 500 is subjected to the multiband imaging in the imaging device 10, whereby the color image of the object SP is displayed on the display unit 160.

Sixth Embodiment

Figure 19:
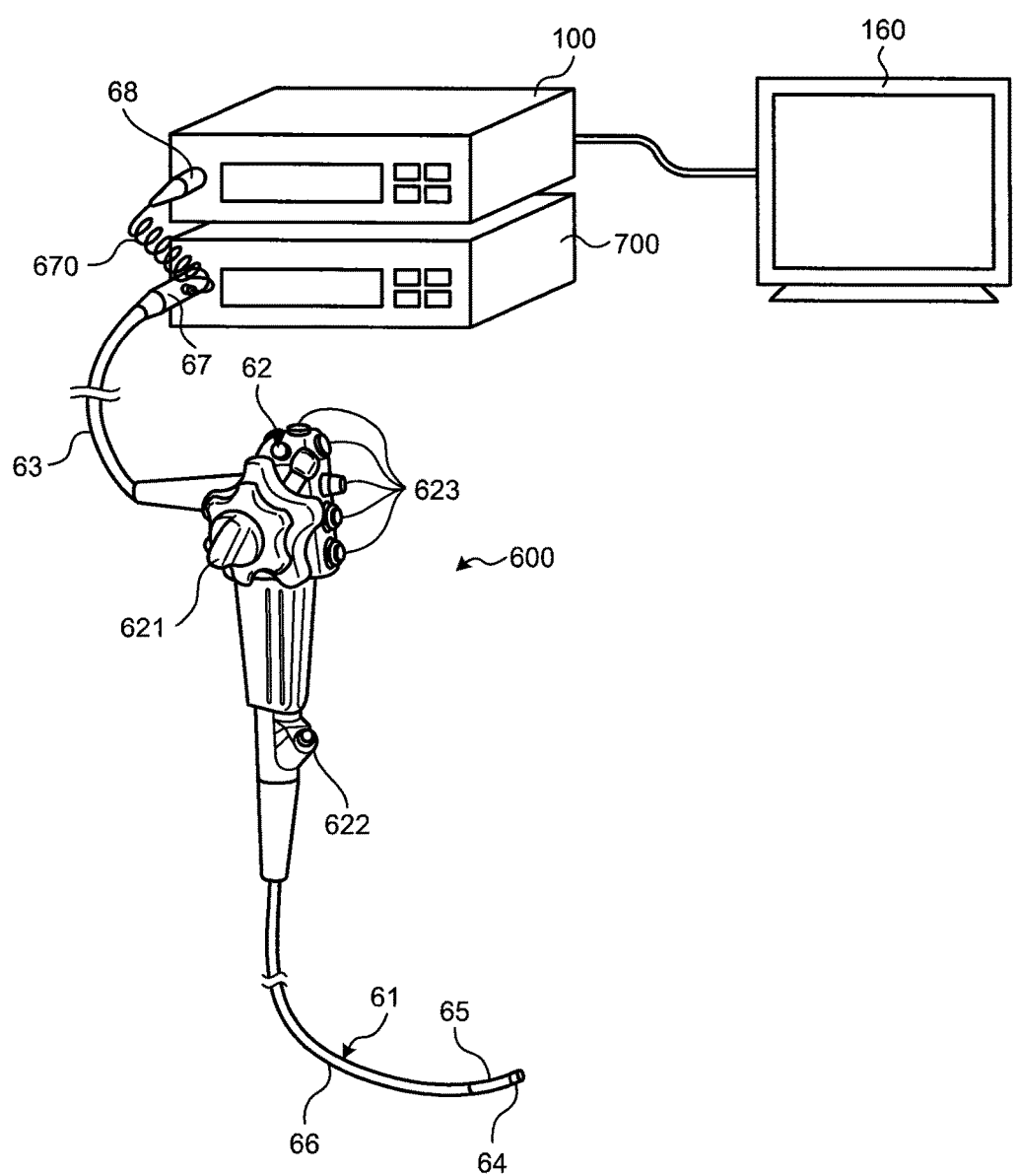
FIG. 19 is a schematic diagram illustrating an exemplary configuration of an imaging system according to a sixth embodiment of the present disclosure.

Next, a sixth embodiment of the present disclosure will be described. FIG. 19 is a schematic diagram illustrating an endoscope system as an exemplary configuration of an imaging system according to the sixth embodiment of the present disclosure. The endoscope system 6 illustrated in FIG. 19 includes the image processing device 100, an endoscope 600, and a light source device 700. The endoscope 600 generates an image of the inside of a lumen in such a manner that a distal end portion is inserted into the lumen of a living body to capture the image. The light source device 700 generates illumination light that is emitted from a distal end of the endoscope 600. The image processing device 100 performs, on the image generated by the endoscope 600, a predetermined image process that is similar to that in the above-mentioned first embodiment. The image processing device 100 also comprehensively controls operation of the entire endoscope system 6. In place of the image processing device 100, the image processing devices 200, 300, and 400 according to the second to fourth embodiments may be applied. In FIG. 19, the display unit 160 (refer to FIG. 1) provided in the image processing device 100 is illustrated on the outside of a main body.

The endoscope 600 includes an insertion portion 61, an operating unit 62, and a universal code 63. The insertion portion 61 has a flexible elongated shape. The operating unit 62 is connected to a proximal end side of the insertion portion 61 to accept input of various operation signals. The universal code 63 extends from the operating unit 62 in a direction different from a direction in which the insertion portion 61 extends. Various cables connected to the image processing device 100 and the light source device 700 are incorporated in the universal code 63.

The insertion portion 61 has a distal end portion 64, a curve portion 65, and a flexible pipe 66. The curve portion 65 incudes a plurality of curve pieces so as to be freely curved. The flexible pipe 66 is connected to a proximal end side of the curve portion 65, and has a flexible elongate shape. The distal end portion 64 of the insertion portion 61 is provided with an optical system and an imaging sensor configured to collect light that comes in from the outside.

An aggregated cable into which a plurality of signal lines is combined is connected between the operating unit 62 and the distal end portion 64. The plurality of signal lines sends and receives electric signals to and from the image processing device 100. In the plurality of signal lines, for example, a signal line that transmits, to the image processing device 100, a video signal (image data) output from the imaging sensor, and a signal line that transmits, to the imaging sensor, a control signal output from the image processing device 100 are included.

The operating unit 62 has a curve knob 621, a treatment tool insertion portion 622, and a plurality of switches 623. The curve knob 621 curves the curve portion 65 in an up-down direction and a left-right direction. A treatment tool such as a biopsy needle, living body forceps, a laser scalpel, and an examination probe is inserted into the treatment tool insertion portion 622. The plurality of switches 623 serves as an operation input unit through which an operation instruction signal is input to a peripheral device such as an air supply unit, a water supply unit, and a gas supply unit as well as the image processing device 100 and the light source device 700.

A light guide and the aggregated cable are at least incorporated in the universal code 63. At an end portion of the universal code 63 on a side different from the side connected to the operating unit 62, a connector unit 67 and an electric connector unit 68 are provided. The connector unit 67 is freely attached to and detached from the light source device 700. The electric connector unit 68 is electrically connected to the connector unit 67 via a coil cable 670 having a coil shape, and freely attached to and detached from the image processing device 100.

The image processing device 100 generates the image to be displayed on the display unit 160 based on the image data output from the imaging sensor provided at the distal end portion 64.

Under the control of the control unit 120 (refer to FIG. 1), the light source device 700 sequentially generates beams of light in the respective four or more wavelength bands into which the visible light region is separated, and irradiates the inside of the lumen from a distal end of the distal end portion 64 through the light guide.

The above-mentioned sixth embodiment has described the example in which the imaging system illustrated in FIG. 1, 6, 10, or 14 is applied to the endoscope system for the living body. Alternatively, the imaging system illustrated in FIG. 1, 6, 10, or 14 may be applied to an endoscope system for industrial purposes. Alternatively, the imaging system illustrated in FIG. 1, 6, 10, or 14 may be applied to a capsule endoscope that is introduced into a living body to capture an image while moving through the inside of the living body.

In addition, the multiband imaging may be performed in such a manner that a light source device that generates white light is provided in place of the light source device 700, a plurality of optical filters having different spectral characteristics is provided at the distal end portion 64 of the endoscope 600, the inside of the lumen is irradiated with the white light, and reflected light from the inside of the lumen is received through the optical filter.

The present disclosure is not limited to each of the above-mentioned first to sixth embodiments as it is. A plurality of components disclosed in the respective first to sixth embodiments can be appropriately combined to form various inventions. For example, some components may be excluded from all the components described in the first to sixth embodiments to form the invention. Alternatively, components described in the different embodiments may be appropriately combined to form the invention.

According to the present disclosure, the deformed images are created in such a manner that the individual images included in the multiband image generated using the frame sequential method are subjected to the image conversion by cumulatively using the items of conversion information between the images adjacent to each other when the images are arranged such that at least the wavelength bands at the time of capturing the images or the positions in the capturing order are adjacent to each other. Then, the color image is created using these deformed images. Therefore, the position adjustment between the images can be suitably performed without the need for complicated prior processes, and the color image with the reduced color deviation and blur can be generated.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing device comprising:
a reference image selector configured to select one image of an image group as a reference image, the image group including four or more images generated in such a manner that an object is sequentially captured separately in four or more different wavelength bands;
a processing target image selector configured to select, as a processing target image, each of a plurality of images of the image group other than the reference image;
an arrangement order setting unit configured to set arrangement order of the images included in the image group such that at least the wavelength bands at the time of capturing the images or positions in capturing order are adjacent to each other between the adjacent images;
a conversion information estimation unit configured to estimate conversion information between the images adjacent to each other when the images included in the image group are arrayed in the arrangement order;
a deformed image creation unit configured to create a deformed image by subjecting the processing target image to an image conversion using the conversion information cumulatively from the processing target image to the reference image in the arrangement order; and
a color image creation unit configured to create a color image using a plurality of the deformed images created based on the respective plurality of images and the reference image.

2. The image processing device according to claim 1, wherein
in the arrangement order, a center wavelength of the wavelength band of the image monotonically shifts from a short wavelength side to a long wavelength side or from the long wavelength side to the short wavelength side.

3. The image processing device according to claim 1, wherein
the arrangement order is set for each of the processing target images selected by the processing target image selector.

4. The image processing device according to claim 1, wherein
the arrangement order is set in common among the respective processing target images selected by the processing target image selector.

5. The image processing device according to claim 1, wherein
the image group includes a plurality of images generated within a predetermined period of time including a reference time among the sequence of images generated in such a manner that the object is sequentially captured separately in the four or more wavelength bands,
the reference image selector selects an image generated at the reference time as the reference image, and
the image processing device further includes:
a control unit configured to control the capturing order such that the images included in the image group are captured in the arrangement order; and
a moving image creation unit configured to create a moving image using a plurality of the color images created based on a respective plurality of the image groups having different reference times.

6. The image processing device according to claim 1, wherein
at least one different wavelength band is inserted between a shortest wavelength band and a longest wavelength band among the four or more wavelength bands in the arrangement order.

7. The image processing device according to claim 1, wherein
in the arrangement order, the wavelength band of the image reciprocates at least once between a shortest wavelength band and a longest wavelength band among the four or more wavelength bands.

8. The image processing device according to claim 1, further comprising:
an interpolation image creation unit configured to create an interpolation image at a reference time using two images in a same wavelength band generated before and after the reference time; and
an interpolation image sequence creation unit configured to set the arrangement order for an image set including the four or more interpolation images created for the respective four or more wavelength bands and an image generated at the reference time such that the wavelength bands are adjacent to each other between the adjacent images, wherein
the reference image selector selects the image generated at the reference time as the reference image,
the processing target image selector selects the interpolation image included in the image set as the processing target image,
the conversion information estimation unit estimates the conversion information assuming that the image set is the image group,
the deformed image creation unit creates the deformed image by subjecting the interpolation image to the image conversion, and the image processing device further includes a moving image creation unit configured to create a moving image using a plurality of the color images created based on a respective plurality of the image sets having different reference times.

9. The image processing device according to claim 1, wherein
the image conversion is any of or a combination of a non-rigid conversion, a plane projection conversion, an affine conversion, a linear conversion, a scale conversion, a rotation conversion, and a translation.

10. The image processing device according to claim 1, wherein
the deformed image creation unit creates the deformed image by cumulating the conversion information sequentially from the processing target image to the reference image in the arrangement order to calculate cumulative conversion information, and subjecting the processing target image to the image conversion using the cumulative conversion information.

11. An image processing device comprising:
a reference image selector configured to select one image of an image group as a reference image, the image group including four or more images generated in such a manner that an object is sequentially captured separately in four or more different wavelength bands;
a processing target image selector configured to select, as a processing target image, each of a plurality of images of the image group other than the reference image;
an arrangement order setting unit configured to set arrangement order of the images included in the image group such that at least the wavelength bands at the time of capturing the images or positions in capturing order are adjacent to each other between the adjacent images;
a conversion information estimation unit configured to estimate conversion information using the images included in the image group sequentially from the processing target image to the reference image in the arrangement order;
a deformed image creation unit configured to create a deformed image by subjecting the processing target image to an image conversion by sequentially using the conversion information estimated by the conversion information estimation unit; and
a color image creation unit configured to create a color image using a plurality of the deformed images created based on the respective plurality of images and the reference image, wherein
the conversion information estimation unit estimates the conversion information between the image included in the image group and the image subjected to the image conversion by the deformed image creation unit.

12. An image processing method comprising:
selecting one image of an image group as a reference image, the image group including four or more images generated in such a manner that an object is sequentially captured separately in four or more different wavelength bands;
selecting, as a processing target image, each of a plurality of images of the image group other than the reference image;
setting arrangement order of the images included in the image group such that at least the wavelength bands at the time of capturing the images or positions in capturing order are adjacent to each other between the adjacent images;
estimating conversion information between the images adjacent to each other when the images included in the image group are arrayed in the arrangement order;
creating a deformed image by subjecting the processing target image to an image conversion using the conversion information cumulatively from the processing target image to the reference image in the arrangement order; and
creating a color image using a plurality of the deformed images created based on the respective plurality of images and the reference image.

13. A non-transitory computer readable recording medium on which an executable computer program is recorded, wherein the computer program instructs a processor of a device to execute:
selecting one image of an image group as a reference image, the image group including four or more images generated in such a manner that an object is sequentially captured separately in four or more different wavelength bands;
selecting, as a processing target image, each of a plurality of images of the image group other than the reference image;
setting arrangement order of the images included in the image group such that at least the wavelength bands at the time of capturing the images or positions in capturing order are adjacent to each other between the adjacent images;
estimating conversion information between the images adjacent to each other when the images included in the image group are arrayed in the arrangement order;
creating a deformed image by subjecting the processing target image to an image conversion using the conversion information cumulatively from the processing target image to the reference image in the arrangement order; and
creating a color image using a plurality of the deformed images created based on the respective plurality of images and the reference image.

14. An imaging system comprising:
an image processing device including:
a reference image selector configured to select one image of an image group as a reference image, the image group including four or more images generated in such a manner that an object is sequentially captured separately in four or more different wavelength bands;
a processing target image selector configured to select, as a processing target image, each of a plurality of images of the image group other than the reference image;
an arrangement order setting unit configured to set arrangement order of the images included in the image group such that at least the wavelength bands at the time of capturing the images or positions in capturing order are adjacent to each other between the adjacent images;
a conversion information estimation unit configured to estimate conversion information between the images adjacent to each other when the images included in the image group are arrayed in the arrangement order;
a deformed image creation unit configured to create a deformed image by subjecting the processing target image to an image conversion using the conversion information cumulatively from the processing target image to the reference image in the arrangement order; and a color image creation unit configured to create a color image using a plurality of the deformed images created based on the respective plurality of images and the reference image; and an imaging unit configured to generate image data by capturing images separately in the four or more wavelength bands using a frame sequential method, and output the image data to the image processing device.

15. The imaging system according to claim 14, wherein the imaging unit includes:

an imaging sensor having a light receiving surface that receives observation light from the object, and configured to output the image data that depend on intensity of the light that has entered the light receiving surface; and a filter unit configured to sequentially dispose, on the light receiving surface, filters having degrees of sensitivity corresponding to the respective four or more wavelength bands.

16. The imaging system according to claim 14, wherein the imaging unit includes:

a light irradiation unit configured to sequentially irradiate the object with beams of light in bands that are limited to the respective four or more wavelength bands; and an imaging sensor having a light receiving surface that receives observation light from the object, and configured to output the image data that depend on intensity of the light that has entered the light receiving surface.

* * * * *